(12) United States Patent
Witschey et al.

(10) Patent No.: US 12,004,882 B2
(45) Date of Patent: Jun. 11, 2024

(54) METHOD AND DEVICE FOR MAGNETIC RESONANCE IMAGING DATA ACQUISITION GUIDED BY PHYSIOLOGIC FEEDBACK

(71) Applicant: The Trustees of The University of Pennsylvania, Philadelphia, PA (US)

(72) Inventors: Walter R. T. Witschey, Philadelphia, PA (US); Francisco Contijoch, San Diego, CA (US); Mark A. Elliott, Bryn Mawr, PA (US); Eugene E. Gualtieri, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/522,098

(22) PCT Filed: Oct. 27, 2015

(86) PCT No.: PCT/US2015/057581
§ 371 (c)(1),
(2) Date: Apr. 26, 2017

(87) PCT Pub. No.: WO2016/069602
PCT Pub. Date: May 6, 2016

(65) Prior Publication Data
US 2017/0332981 A1 Nov. 23, 2017

Related U.S. Application Data

(60) Provisional application No. 62/073,183, filed on Oct. 31, 2014.

(51) Int. Cl.
*A61B 5/00* (2006.01)
*A61B 5/055* (2006.01)
(Continued)

(52) U.S. Cl.
CPC .......... *A61B 5/7289* (2013.01); *A61B 5/0044* (2013.01); *A61B 5/055* (2013.01);
(Continued)

(58) Field of Classification Search
CPC ... A61B 5/7289; A61B 5/0402; A61B 5/0044; A61B 5/055; A61B 2576/023;
(Continued)

(56) References Cited

U.S. PATENT DOCUMENTS 5,997,883 A * 12/1999 Epstein ................ A61B 5/7292
324/306
6,230,039 B1 5/2001 Stuber et al.
(Continued)

OTHER PUBLICATIONS

Lenz et al., "Retrospective cardiac gating: A review of technical aspects and future directions", Magnetic Resonance Imaging, Sep.-Oct. 1989, vol. 7, Issue 5, 445-455.
(Continued)

*Primary Examiner* — Joseph M Santos Rodriguez
*Assistant Examiner* — Amy Shafqat
(74) *Attorney, Agent, or Firm* — BakerHostetler

(57) ABSTRACT

An adaptive real-time radial k-space sampling trajectory (ARKS) can respond to a physiologic feedback signal to reduce motion effects and ensure sampling uniformity. In this adaptive k-space sampling strategy, the most recent signals from an ECG waveform can be continuously matched to the previous signal history, new radial k-space locations were determined, and these MR signals combined using multi-shot or single-shot radial acquisition schemes. The disclosed methods allow for improved MRI imaging.

20 Claims, 19 Drawing Sheets
(7 of 19 Drawing Sheet(s) Filed in Color)

(51) Int. Cl.
*A61B 5/33* (2021.01)
*G01R 33/48* (2006.01)
*G01R 33/563* (2006.01)
*G01R 33/567* (2006.01)

(52) U.S. Cl.
CPC ............ *A61B 5/33* (2021.01); *G01R 33/5673* (2013.01); *A61B 2576/023* (2013.01); *G01R 33/4824* (2013.01); *G01R 33/56325* (2013.01)

(58) Field of Classification Search
CPC ....... A61B 2576/02; A61B 5/04; A61B 5/042; A61B 5/0428; A61B 5/7292; A61B 5/318; A61B 5/352; A61B 5/0263; A61B 5/7285; G01R 33/5673; G01R 33/56325; G01R 33/4824; G01R 33/5635; G01R 33/56308; G01R 33/4826; G01R 33/481885; G01R 33/4818; G01R 33/567; G01R 33/5676; G01R 33/56366; G06T 2207/30104; G01F 1/716
See application file for complete search history.

(56) References Cited

U.S. PATENT DOCUMENTS

| | | | | |
|---|---|---|---|---|
| 2002/0156366 | A1* | 10/2002 | Stainsby | A61B 5/055 600/413 |
| 2005/0245812 | A1* | 11/2005 | Kim | A61B 5/055 600/410 |
| 2006/0224062 | A1* | 10/2006 | Aggarwal | G01R 33/5673 600/413 |
| 2010/0277173 | A1* | 11/2010 | Landschuetz | G01R 33/5673 324/309 |
| 2011/0095762 | A1 | 4/2011 | Piccini et al. | |
| 2013/0285655 | A1* | 10/2013 | Miyazaki | G01R 33/5608 324/309 |
| 2015/0309135 | A1* | 10/2015 | Axel | G01R 33/56509 324/309 |
| 2015/0374237 | A1* | 12/2015 | Hu | A61B 5/7292 600/413 |
| 2016/0047874 | A1* | 2/2016 | Grodzki | G01R 33/5635 324/309 |
| 2016/0310761 | A1* | 10/2016 | Li | G06K 9/52 |
| 2017/0035298 | A1* | 2/2017 | Contijoch | A61B 5/0044 |

OTHER PUBLICATIONS

Bourke, "Cross Correlation—AutoCorrelation—2d Pattern Identification", Aug. 1996, 9 pages.

Contijoch et al., "Continuous adaptive sampling of k-space from real-time physiologic feedback in MRI", Proc. Intl. Soc. Mag. Reson. Med., 2015, 23, p. 2567.

Contijoch et al., "Continuous adaptive radial sampling of k-space from real-time physiologic feedback in MRI", Journal of Cardiovascular Magnetic Resonance, 2015, 17(Suppl 1), P37, 2 pages.

* cited by examiner

METHOD AND DEVICE FOR MAGNETIC RESONANCE IMAGING DATA ACQUISITION GUIDED BY PHYSIOLOGIC FEEDBACK

RELATED APPLICATION

This application claims the benefit of U.S. Provisional Application No. 62/073,183 entitled "Method and Device for Magnetic Resonance Imaging Data Acquisition Guided by Physiologic Feedback", filed Oct. 31, 2014.

GOVERNMENT RIGHTS

The subject matter disclosed herein was made with government support under award number R00-HL108157 awarded by the National Heart, Lung and Blood Institute, the National Institutes of Health. The Government has certain rights in the herein disclosed subject matter.

BACKGROUND

Magnetic resonance imaging (MRI) is a medical imaging technique used to investigate the anatomy and physiology of the body. MRI scanners use strong magnetic fields and radiofrequency (RF) waves to form images of the body.

Hydrogen nuclei (mainly those within water molecules) in the body are aligned by the strong magnetic field of the MRI device and create a net magnetic moment.

RF pulses from the MRI device affect this magnetic moment. When the radiofrequency pulse ends, the excited hydrogen nuclei relax and emit RF energy that can be detected by the MRI device.

If the scene is periodic, such as the motion of the heart, it is common in MRI to combine data from multiple periods to improve image quality. For example, heart motion can be obtained with electrocardiogram (ECG) triggered imaging. In this method, a segmented, or multi-heartbeat, acquisition is performed. During each heartbeat, a subset of the MRI image data is captured at each phase of the cardiac cycle. After all data subsets have been acquired, this data is combined to produce a series of images that can be displayed as a movie (cine). A cardiac cycle is typically divided into about 20 to 30 segments for the cine video. Each cine image frame is typically composed of information gathered over 5-15 heart beats, allowing for a movie to be acquired within 20 seconds or less.

A problem is that, for a number of cardiac MRI applications, including stress testing, imaging of arrhythmias, and measurement of pressure-volume relationships, there can be significant motion artifacts or contrast variation as a result of inconsistent data between heartbeats, limiting the total amount of acquired data.

The main problem with multiple beat acquisitions is that the human heart exhibits only quasi-periodic motion, so it is not guaranteed that the heart will be in the same position. In general, the RR interval (the period of one heart cycle) exhibits normal fluctuations that depend on a host of sympathetic and parasympathetic systems. For example, the RR interval usually decreases during breath-hold examinations, and the relative duration of diastolic and systolic periods does not change linearly with heart rate. If an arrhythmia occurs, then not only is the heart rate variable, but the loading conditions and contractile state of the heart may vary. This inconsistent motion can result in artifacts and reduced spatial and temporal resolution.

Respiratory motion is an additional problem affecting segmented data acquisitions. Many clinical exams use breath-held examinations or motion-detecting scans to reduce respiratory motion artifacts, but if the breath-held scan time exceeds the patient's endurance, then inconsistent position data can lead to artifacts or reduced spatial resolution. The efficiency of a navigator examination partly determines the overall scan time. If the range of accepted motions of the diaphragm is increased to improve scan efficiency, then the position of the heart and lungs may be inconsistent.

SUMMARY

In one aspect, the present disclosure provides methods of making an image using MRI data of a body part such as the heart or lungs that undergoes periodic motion. Physiologic data such as an ECG or other cardiac signal or a respiratory signal can be analyzed to determine previous times that the body part was in a similar position to a current position. For example, an autocorrelation on the physiologic data can be done to determine these previous times.

The MRI hardware-controllable settings used at the previous times can be analyzed to determine a new set of MRI hardware-controllable settings. The MRI hardware-controllable settings can be the settings to manipulate the magnetic fields and radiofrequency pulses of the MRI and can correspond to k-space data that are an abstraction of the time domain MRI signal.

In another aspect, the new set of MRI hardware-controllable settings can be such that the k-space values for the total set of MRI hardware-controllable settings is well distributed.

The body part can be scanned with the new MRI hardware-controllable settings to produce new MRI data. The new MRI data along with the previous data from the previous times can be used to produce an MRI image.

These and other characteristic features of the invention will be apparent from the following detailed description of the invention.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. The patent or application file contains at least one drawing executed in color. Copies of this patent or patent application publication with color drawing(s) will be provided by the Office upon request and payment of the necessary fee. In the drawings.

DETAILED DESCRIPTION OF ILLUSTRATIVE EMBODIMENTS

Figure 1A:
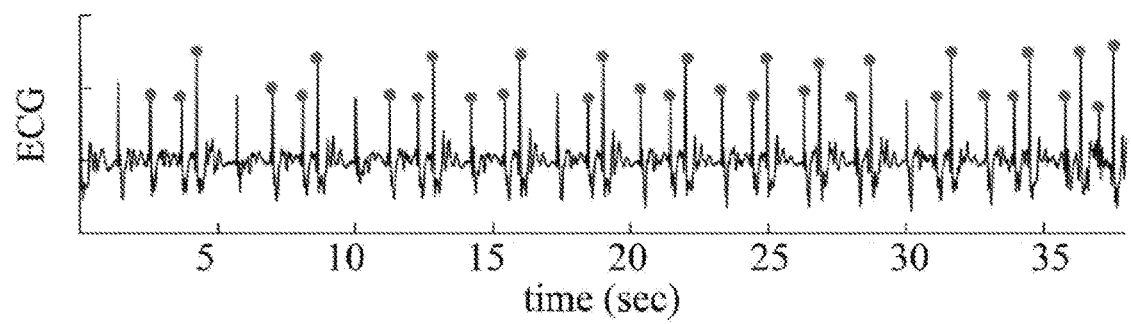
FIGS. 1A-C illustrate acquisition of retrospective cine MRI k-space data during a severe arrhythmia and using arrhythmia rejection.

Certain specific details are set forth in the following description with respect to the attached figures to provide a thorough understanding of various embodiments of the invention. Certain well-known details are not set forth in the following disclosure, however, to avoid unnecessarily obscuring the various embodiments of the invention. Those of ordinary skill in the relevant art will understand that they can practice other embodiments of the invention without one or more of the details described below. Also, while various methods are described with reference to steps and sequences in the following disclosure, the description is intended to provide a clear implementation of embodiments of the invention, and the steps and sequences of steps should not be taken as required to practice the invention.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the claimed subject matter. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the disclosed subject matter which are, for clarity, described herein in the context of separate embodiments, can also be provided in combination in a single embodiment. Conversely, various features of the disclosed subject matter that are, for brevity, described in the context of a single embodiment, can also be provided separately or in any subcombination. Further, reference to values stated in ranges includes each and every value within that range. Any documents cited herein are incorporated herein by reference in their entireties for any and all purposes.

It is desirable to reduce artifacts associated with motion by adapting the acquisition dynamically in response to changes in physiology. In conventional MRI acquisitions, adaptive sampling is used to capture the motion of, for instance, the beating heart. In MRI, data is sampled in the multidimensional Fourier domain, called k-space. Typically, in clinical cardiac cine examinations, new k-space data is acquired when an R-wave is detected from the ECG physiologic waveform, permitting complete acquisition of k-space in several heartbeats.

In most cardiac cine exams, the transition from one part of k-space to the next occurs within a few milliseconds after detection of the R-wave. This approach is common to both retrospective and prospective cardiac gating.

An example of gating is described in Lenz, et al. Retrospective cardiac gating: a review of technical aspects and future directions. Magn Reson Imaging 7:445-455 1989. Another example of adaptive k-space sampling is when, during an arrhythmia, data is rejected if the RR interval falls outside of a previously specified range (arrhythmia rejection). The decision to reject and reacquire data occurs within a few milliseconds.

In both retro- and prospectively-gated examinations, with or without arrhythmia rejection, the sampling trajectory updates occur relatively infrequently, usually once every heartbeat. As a result, they are not well designed to respond correctly or quickly, if at all, to more complex signals, such as heart rate variations, arrhythmias, dynamic challenges or contrast changes and result in inconsistent motion and artifacts.

When ectopy does occur during a retrospective examination, arrhythmia rejection is used to discard inconsistent data and reacquire it during the next normal period. Arrhythmia rejection is not always desirable since useful information about cardiac ectopy and true ventricular function is lost. Moreover, as is shown in FIG. 1, there are situations in fact where there is no normal sinus rhythm and retrospective cine MRI would fail to correctly synthesize data based on the time from the R-wave alone or if the correct R-wave was not detected correctly. These retrospective MRI scans are not able to adapt to physiologic changes because the motion is no longer consistent between periods, so the entire data set must be reacquired under the new physiologic condition.

Figure 1B:
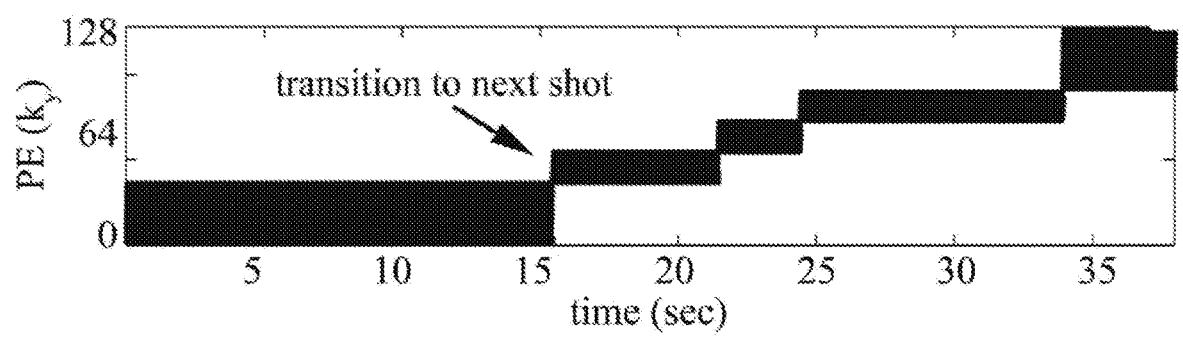
Figure 1C:
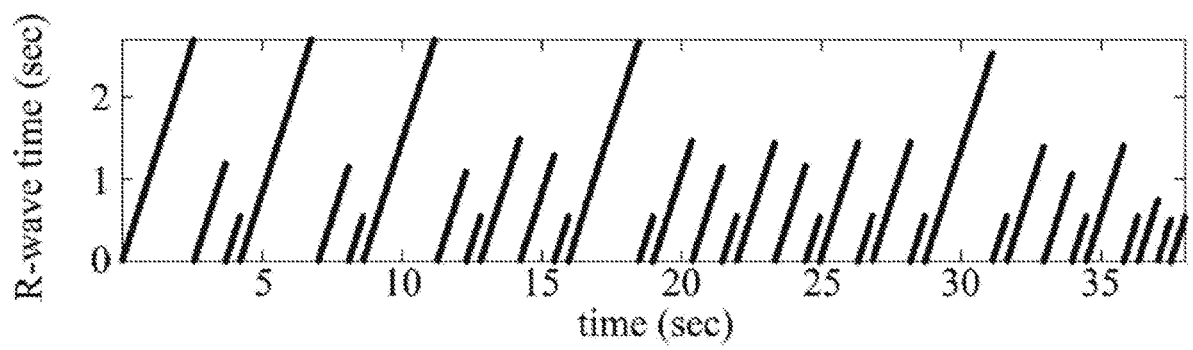

FIGS. 1A-C illustrate the conventional acquisition of retrospective cine MRI k-space data during a severe arrhythmia and using arrhythmia rejection. In FIG. 1A, ECG data is continuously acquired and R-waves (dots) are detected. In FIG. 1B, after each detected R-wave, $N_{k_y}$ segments of k-space are collected until, after a number of periods, all 128 $k_y$ phase encodes (PE) are collected.

For a normal subject in sinus rhythm, the transition from one $N_{k_y}$ to the next occurs after each R-wave is detected. For this patient with a severe arrhythmia, the inconsistent RR-interval causes these $N_{k_y}$ data to be rejected and reacquired during the subsequent, detected RR interval. There may be a number of problems with this type of acquisition, such as 1) the R-wave may not be detected; 2) the total time to acquire all k-space data may exceed the time the patient can hold their breath; or 3) even when the RR-interval is approximately the same, the accepted data may not be consistent because of variations in preload (diastolic filling). These problems may cause motion artifacts since the beat-to-beat data is inconsistent.

In FIG. 1C, a plot of the time from the last detected R-wave to the next clearly shows that the acquisition time and detected RR-interval is not consistent.

Figure 2:
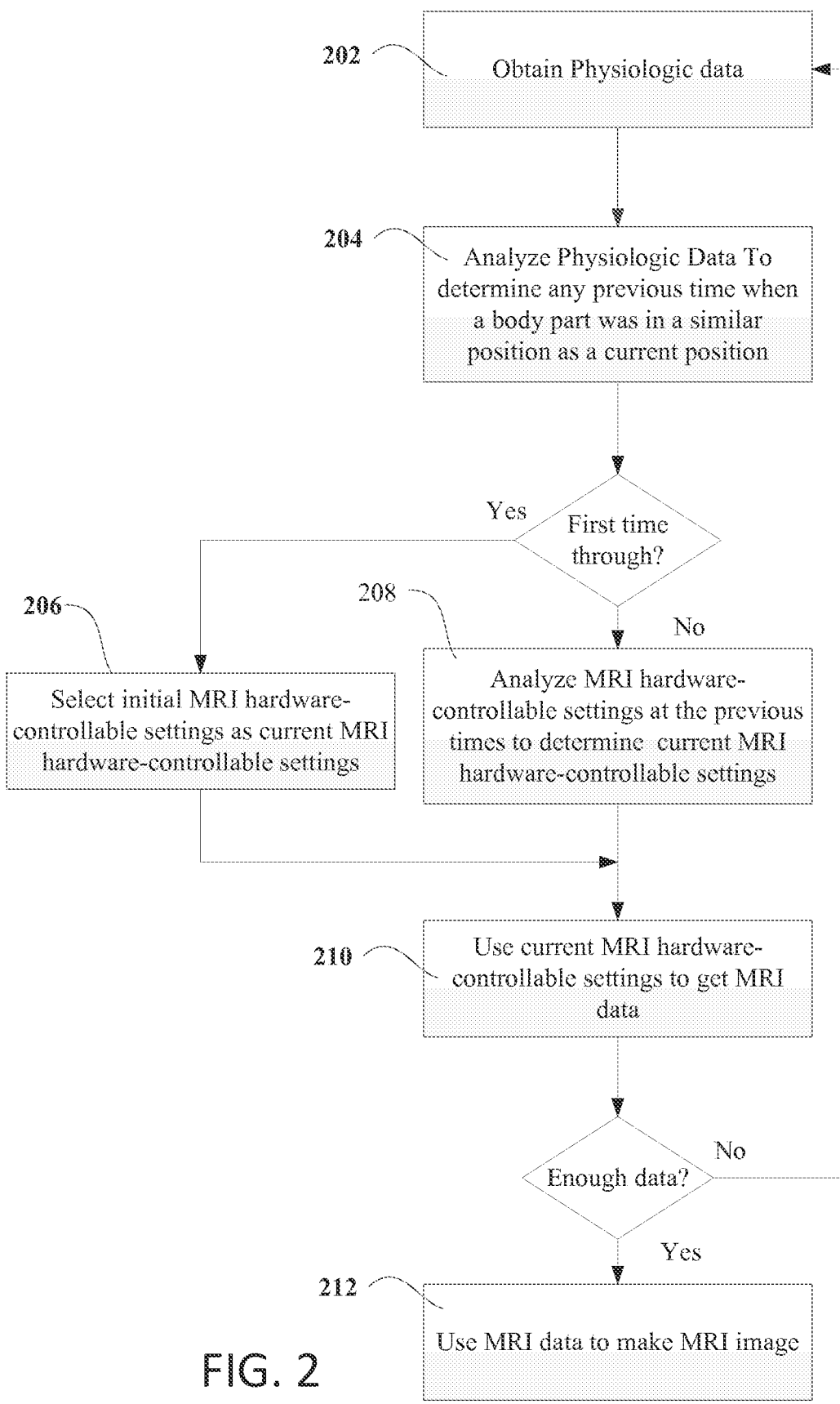
FIG. 2 is a flow chart of a method for magnetic resonance imaging data acquisition guided by physiologic feedback of one embodiment.

FIG. 2 illustrates a method for magnetic resonance imaging data acquisition guided by physiologic feedback of one embodiment.

In step 202, physiologic data is obtained. The physiologic data can be a cardiac signal such as an ECG, a respiratory signal, or some other physiological signal.

In step 204, the physiologic data is analyzed to determine any previous time when a body part was in a similar position as a current position. The body part is suitably a body part—such as the heart or lungs—that undergoes periodic motion. In one embodiment, an autocorrelation on the physiologic data can be done to determine the previous times.

MRI hardware-controllable settings can be the settings to manipulate the magnetic fields and RF pulses of the MRI. The hardware-controllable settings govern the way that the MRI device operates. The MRI hardware-controllable settings can correspond to k-space values that are an abstraction of the time domain MRI signal.

If it is the first time through an MRI process and there are no previous matching times, in step 206, initial MRI hardware-controllable settings can be selected as the current MRI hardware-controllable settings.

Otherwise in step 208, MRI hardware-controllable settings at the previous times are analyzed to determine the current MRI hardware-controllable settings. For example, a new set of MRI hardware-controllable settings can be such that the k-space values for the total set of MRI hardware-controllable settings is well-distributed.

In step 210, the body part can be scanned with the new MRI hardware-controllable settings to produce new MRI data. In this pass-through, the new MRI hardware-controllable settings are selected as the current MRI hardware-controllable settings.

If there is enough data acquired, in step 212, the new MRI data along with the previous data from the previous times can be used to produce an MRI image.

As described below, in one embodiment, MRI acquisition may be continuously adapting in response to a real-time physiologic feedback signal. This method may be termed Adaptive Real-Time k-space Sampling (ARKS). In this method, the most recent signal is continuously compared to its history and data obtained from previous periods are used to determine how subsequent data is acquired.

There are a number of advantages to this type of approach: 1) adaptive sampling produces a near-optimal sampling scheme, improving signal-to-noise and reducing artifact levels; 2) can be configured to produce real-time image display; and 3) mitigates deleterious motion artifacts by adapting to a physiologic signal. This approach to k-space sampling has benefits for clinical examinations of the heart and other body parts.

In one embodiment, a method for MRI can continuously adapt a radial k-space sampling trajectory to changes in physiology and maximize motion consistency between periods using a physiologic feedback signal. In this embodiment, a new radial k-space projection is chosen adaptively, in real-time, and not according to a predefined schedule.

In another embodiment, a method for MRI can continuously adapt a Cartesian k-space sampling trajectory to changes in physiology and maximize motion consistency between periods using a physiologic feedback signal. In this embodiment, a new Cartesian phase-encoding trajectory is chosen adaptively, in real-time, and not according to a predefined schedule. Other k-space trajectories such as spiral sampling may be similarly adapted in real-time in response to the physiologic signal.

One application of this method is improving cardiovascular MRI image examinations by combining new data with additional data from previous periods to improve image quality, guaranteeing that the sampling trajectory is uniform, reducing Nyquist undersampling artifacts, and permitting continuous image re-construction and display in real-time. Although commonly used prospective and retrospective cardiac MRI exams do respond to changes in physiology, images are reconstructed and shown only after all data from multiple periods are collected, and, it is usually only a single signal (detection of the R-wave) that is used to inform changes to the k-space trajectory and gradients G for spatial encoding. A disadvantage of infrequent, once-per-period k-space sampling trajectory updates is they cannot react quickly to complex changes in physiology, such as heart rate variations, arrhythmias, or respiration.

The present methods also share the benefits of retrospective MRI scans, including continuous collection of imaging data for reconstruction of all cardiac phases, including late and end-diastole, image display in smooth, continuous cine loop, and uninterrupted RF excitation, so that the magnetization reaches a steady-state, reducing transient fluctuations of the measured signal (lightning artifact), and sharing of data across multiple periods to improve image quality. A major advantage of the method of acquisition described herein is that is that data can be continuously reconstructed and displayed in real-time.

There is considerable interest to collect and reconstruct MRI data in real-time because this altogether avoids the problem of inconsistent motion between periods. In real-time MRI, only consecutive temporal data is combined to form an image, but an important problem is to obtain images with sufficient signal-to-noise ratio and spatial resolution from limited data, without sacrificing intra-period temporal resolution. Recent advances in multiple detector (parallel) imaging and compressed sensing data reconstruction permit high quality images to be reconstructed from k-space data sampled far below the Nyquist limit. Nevertheless, it is generally recognized that reconstructing data across multiple periods would provide higher image quality if the motion is consistent across periods. The method of one embodiment can continuously adapt to the physiologic signal and uses information from previous periods to optimize the uniformity of the sampling trajectory at all times. The method has the advantages of both real-time, in that images are shown continuously to the viewer as the data is collected, and multiple period data sampling, in that additional data is used to reconstruct images at higher signal-to-noise ratio and spatial resolution.

Without being bound to any particular theory, it is unclear that real-time exams can be performed with adequate spatiotemporal resolution with 3D coverage without a multi-period sampling approach. Hence, for 3D spatial encoding trajectories, the disclosed methods are attractive because they offer both real-time display and 3D coverage.

In MRI, the measured signal s is related to the object water $^1$H spin density by the Fourier transform:

$$s(k) = \int_{-\infty}^{\infty} \rho(x) e^{-ik \cdot x} dx, \tag{1}$$

where the object is spatially-encoded at k-space locations k, which are dependent on the magnetic field gradients, G=

$$\left[\frac{\partial B_z}{\partial x}, \frac{\partial B_z}{\partial y}, \frac{\partial B_z}{\partial x}\right], \quad (2)$$

$$k = \gamma \int_\tau^{\tau-T} G(t)dt.$$

Modulation of the magnetic field gradient coil amplitudes G permits sampling of the multidimensional Fourier domain (k-space). For satisfactory reconstruction of ρ, it is important to sample signals uniformly throughout k-space. One practical method is to acquire data along multiple radial projections.

Then, the MR signal equation appears:

$$s(k_r, \theta) = \int_{-\infty}^{\infty} \rho(r, \theta) e^{-i(k_r \cos\theta \hat{x} + k_r \sin\theta \hat{y})} r\, dr\, d\theta, \quad (3)$$

where $k_r$ denote k-space data acquired along the projection and $\theta = \tan^{-1}(G_x/G_y)$ is the polar sampling angle. The radial data is obtained by switching the magnetic field gradients each pulse sequence repetition time (TR).

As is seen further, in one exemplary embodiment, a physiologic signal, such as the ECG waveform from a patient, is measured. This ECG waveform is continuously analyzed and compared to its previous history. Together, the previous ECG signals, as well as the latest one, are used to determine the next polar sampling angle in k-space.

Figure 3:
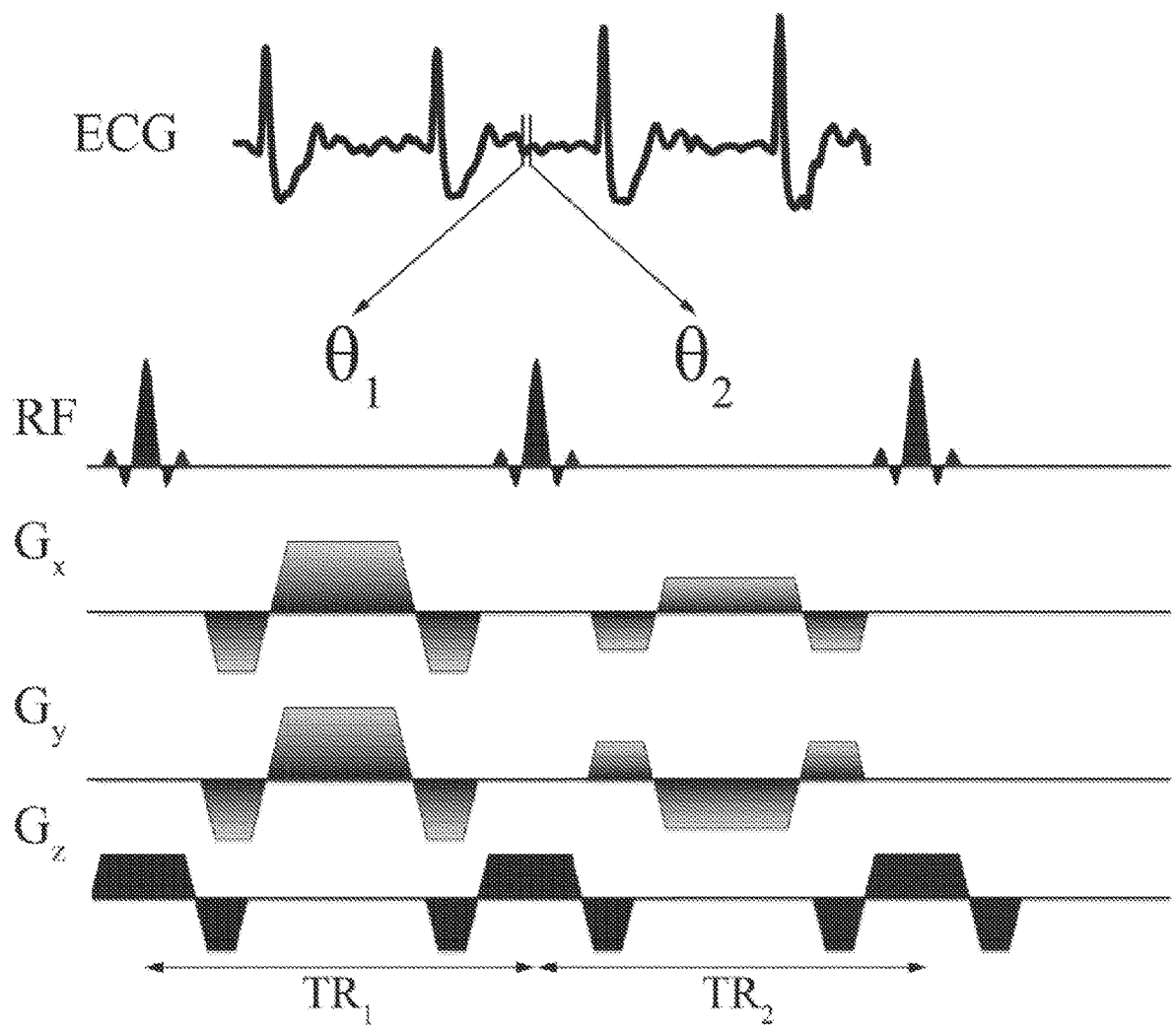
FIG. 3 illustrates a subset of a pulse sequence; depicting two kernels of a balanced steady-state free-precession pulse sequence, for adaptive radial sampling of k-space from an ECG signal.

FIG. 3 illustrates a pulse sequence for an adaptive radial sampling of k-space from an ECG signal. Although radial sampling is used in this disclosed embodiment, other sampling techniques can also be used.

A physiologic signal, e.g. ECG data, is continuously acquired and compared to its previous history. Instructions to acquire a new radial projection $\theta = \tan^{-1}(G_y/G_x)$ are sent from the physiologic signal analysis routine to the measurement controller of the MRI scanner in real-time. RF=radiofrequency pulses, $G_x = \partial B_z/\partial x$ the orthogonal components of the magnetic field gradients, TR=repetition time.

After this angle is determined, the magnetic field gradients G are updated (FIG. 3). This is different from other sampling strategies in that (1) the polar sampling angle is not found via a pre-determined schedule and (2) the polar sampling angle is updated much more often than once each cycle of the physiological signal. For the balanced steady-state free-precession MRI sequence shown in FIG. 3, the polar sampling angle could be updated as often as every few milliseconds. The continuous determination of the polar angle from physiologic data potentially allows the k-space trajectory to respond rapidly to changes in physiology in ways that traditional radial sampling would not allow.

Figure 4:
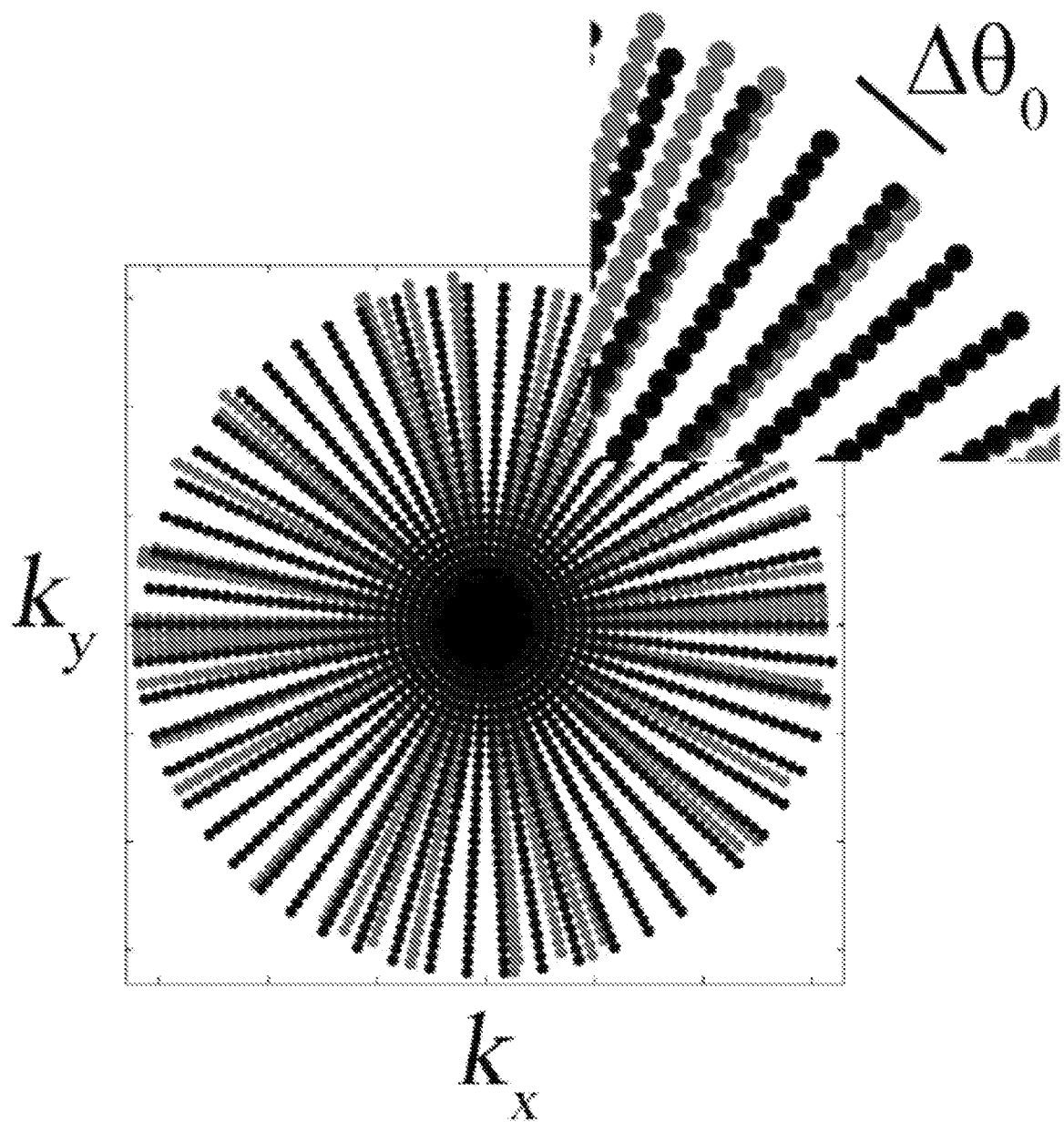
FIG. 4 illustrates a comparison of uniform and non-uniform radial sampling in k-space.

For radial sampling with uniformly-spaced projections, the number of projections $N_\theta$ required to fulfill Nyquist sampling and prevent aliasing of the Fourier signal is $$N_{\theta, Nyquist} = N_r \frac{\pi}{2}, \quad (4)$$

where Nr is the number of samples $k_r$ per projection. The spacing between projections is not uniform in one embodiment and therefore it is not guaranteed that the Nyquist sampling criteria is met for all regions of k-space. Even when the number of projections $N_\theta$ exceeds $N_{Nyquist}$, these projections are not uniformly distributed, so there may be some polar angles that do not satisfy the Nyquist sampling criterion (FIG. 4). Unlike Cartesian k-space sampling, it is (without being bound to any particular theory) usually possible to reconstruct useful images with $N_\theta < N_{Nyquist}$ since radial sampling has different signal aliasing properties. In the next section, it is discussed how the selection of the polar angle is determined to satisfy the Nyquist criteria for all image frames in one embodiment.

FIG. 4 illustrates a comparison of uniform and non-uniform radial sampling uniformity in k-space. In FIG. 4, uniform (black) and random (red/lighter shading) radial sampling are shown. Nyquist sampling is satisfied if the arc $\Delta\theta_0$ is small, however, with random sampling, there may be some polar angles $\ominus$ for which $\Delta\theta_0$ does not satisfy Nyquist sampling in the polar dimension. In general, uniform polar sampling is essential to reduce undersampling artifacts and radial streaks.

FIG. 5 presents an illustrative embodiment of radial k-space sampling. FIGS. 5A-F are diagrams that illustrate how radial projections are adaptively chosen in response to a real-time physiologic signal in one embodiment using a 4-8-29 sampling scheme (shots-segments-projections). In FIG. 5A, a signal buffer $S_S$ with the most recent physiologic data (1-2 heart beats). In FIG. 5B, a large buffer $S_L$ storing a previous history of the physiologic signal is shown. 4 similar periods of the cardiac cycle are labeled (red-lighter shading). In FIG. 5C, cross-correlation between buffers $S_S$ and $S_L$. Local maxima of signal overlap are labeled (red-lighter shading). The negative lags for the first 4 local maxima are used to label the ECG in FIG. 5B. In FIG. 5D, for the first 3 shots, 8 radial projections (segments) are acquired and labeled −4 to 3, with the 0 projection corresponding to the lag index in FIG. 5C. Only 4 projections are acquired in the last shot and together these 28 projections are used to determine the angle 9 of the 29th projection. FIG. 5E, illustrates 29 k-space radial projections. The color of each projection corresponds to the shot index in FIG. 5D. FIG. 5F illustrates simulated reconstructed image for this image frame.

Figure 5A:
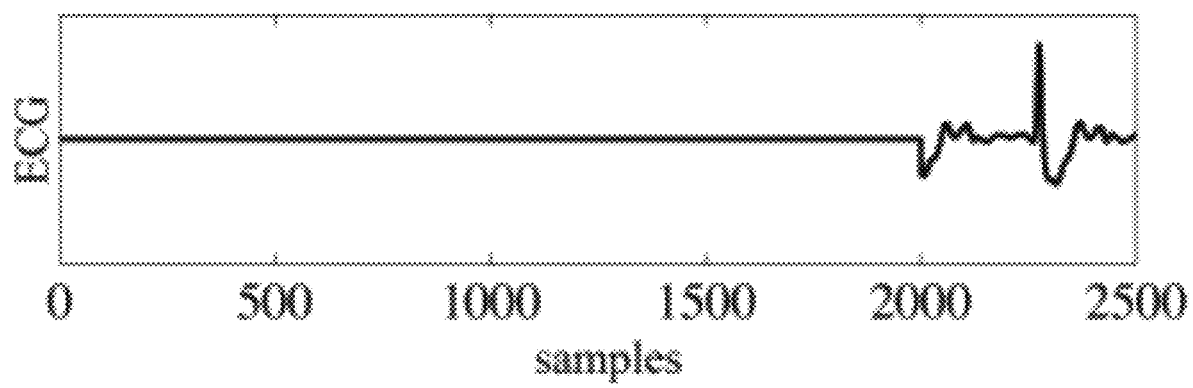
FIGS. 5A-F illustrate how radial projections are adaptively chosen in response to a real-time physiologic signal using a 4-8-29 sampling scheme (shots-segments-projections).
Figure 5B:
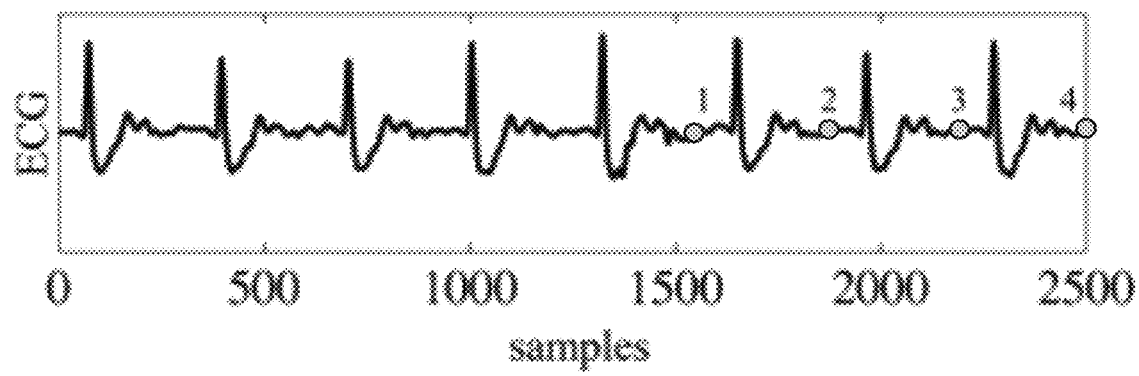

In FIG. 5A, the most recent physiologic signal $S_S$ is stored in a small N×1 buffer in memory. The size of the buffer is chosen to capture sufficient important features of the signal to match to a previously acquired signal. For an ECG signal, the buffer size is large enough to include data from 1-2 heartbeats. In FIG. 5B, a signal sampled for a longer period of time $S_L$ containing a previous record of the physiologic data is stored in a M×1 buffer in memory. The signals $S_S$ and $S_L$ are cross-correlated $$S_S * S_L[n] = \sum_{m=0}^{M-1} S_S[m]S_L[m+n]. \quad (5)$$

Figure 5C:
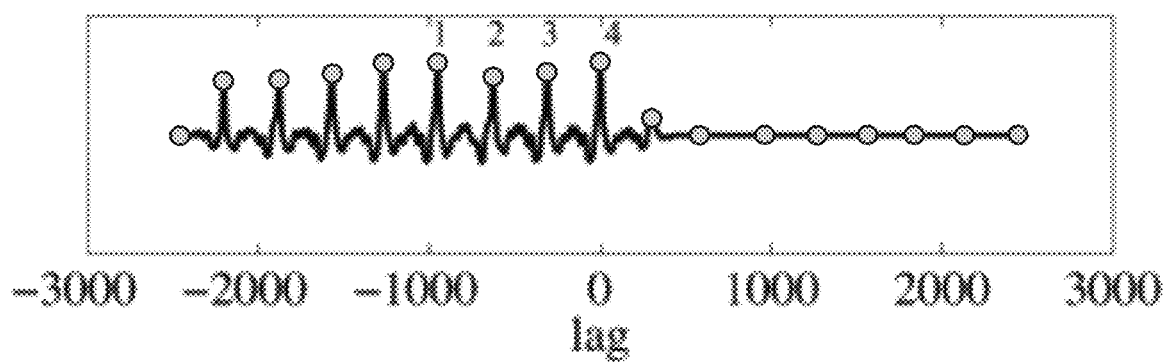

Local maxima are determined from the result of the cross-correlation as shown in FIG. 5C and correspond to the signals highlighted in red in FIG. 5B. The lag n of each local maxima is an index to the maximum overlap of the two signals.

Figure 5D:
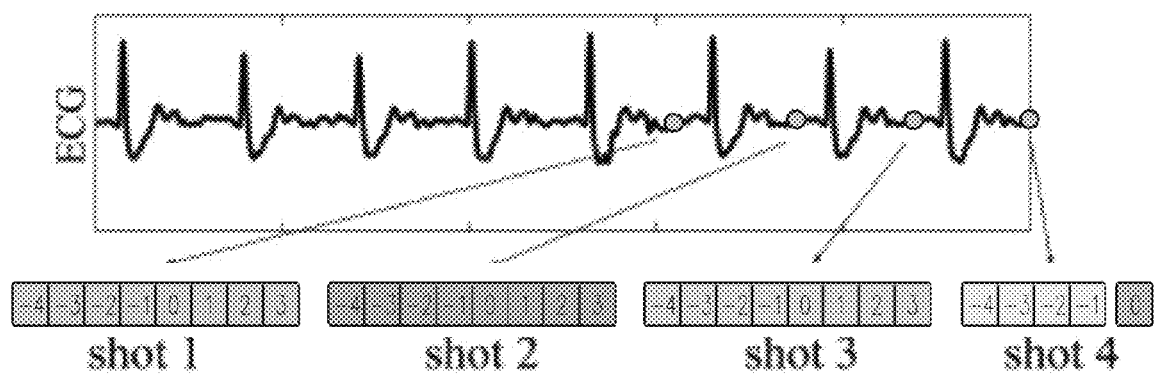

Multiple heartbeat k-space trajectories are specified by the number of radial projections (segments) per heartbeat (shot). An example of how segments and shots are defined in one embodiment as shown in FIG. 5D. In the example shown, the number of segments is 8 and the number of shots is 4. The total number of k-space projections per image frame is $$N_\theta = N_{segments} * N_{shots} - \frac{N_{segments}}{2} + 1. \tag{6}$$

For this example, the total number of projections would be 29. For each shot, the lag corresponding to the local maxima is the center of the segments of k-space views used. Note that the final shot has fewer segments than other shots because future segments have not yet been acquired. It is, however, still possible to acquire more segments during this last shot.

From a list of previously acquired projections, the angles corresponding to the identified segments are collated. The list is sorted in ascending order and the angular differences between adjacent radial projections are computed. For all $\theta \in \mathbb{R}$ on the interval [0 360)

$$\Delta\theta_i = \theta_{i+1} - \theta_i \tag{7}$$

Figure 5E:
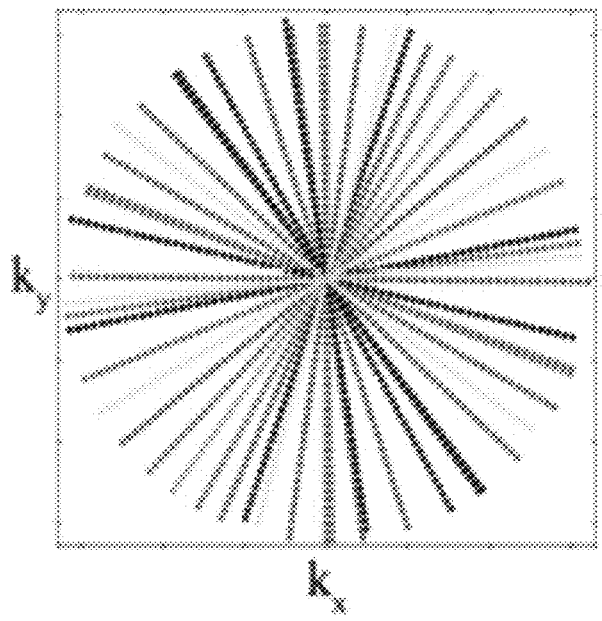
Figure 5F:

The next projection angle is then chosen such that it bisects the largest $\Delta\theta_i$ from the list. Since each new projection fills in the low data regions of k-space, one embodiment provides nearly uniform sampling to the physiology at all times (FIG. 5E).

To determine the uniformity of sampling, k-space trajectories were analyzed with a function x that reports the probability that two adjacent radial projections are separated by a polar angle $\Delta\theta$. $\chi$ is a probability distribution:

$$\chi_i = P(\Delta\theta_i = \theta_{i+1} - \theta_i), \tag{8}$$

where $\Delta\theta$ lies on the interval $(0, \pi]$. The rationale was that, for an optimal k-space trajectory, $\chi$ would resemble an ideal distribution $\chi 0$ and a plausible way to test its performance would be to compare its distribution $\chi$ to the ideal distribution $\chi 0$.

Without being bound to any particular theory, one reasonable function to describe the ideal distribution $\chi 0$ was the Dirac delta function:

$$\chi 0 = \delta(\Delta\theta_i - \Delta\theta_0) \tag{9}$$

Where $\Delta\theta_0 = (\pi/N) \cdot \chi 0$ describes the distribution function for uniformly-spaced radial k-space projections and is unity at $\Delta\theta_0$ and 0 elsewhere (FIG. 6). This distribution is ideal in the sense that k-space is uniformly sampled in the polar dimension $\theta$ and would therefore result in an optimal signal-to-noise ratio and artifact level.

Figure 6A:
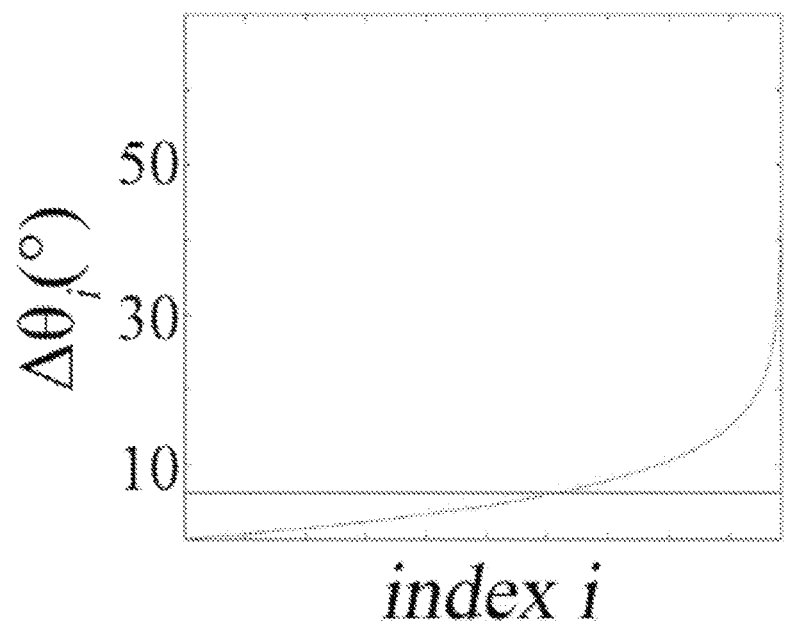
FIGS. 6A-C illustrate an analysis of uniform and random k-space sampling uniformity.
Figure 6B:
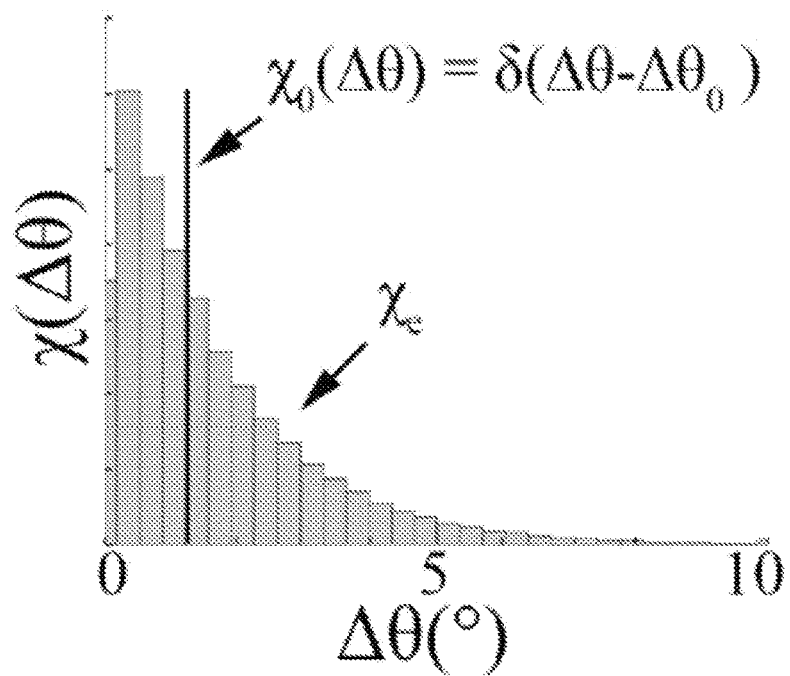
Figure 6C:
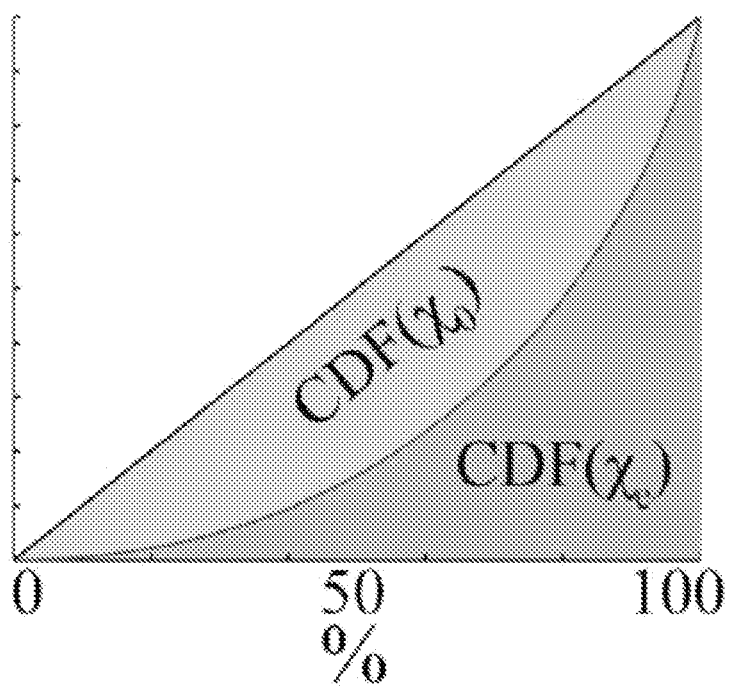

FIGS. 6A-C are diagrams that illustrates an analysis of uniform and random k-space sampling uniformity. FIG. 6A is a graph of sorted angles $\Delta\theta_0$ for uniform (black) and random (red-light shaded) radial sampling trajectories.

FIG. 6B illustrates sampling distributions for uniform (black=0) and random sampling (red=r). The uniform sampling distribution is a delta function positioned at the 180°/$N_c$. FIG. 6C illustrates cumulative distribution functions (CDF) for uniform (black) and random (red-light shaded) radial sampling trajectories. The percent ideal uniformity P is the relative area of any sampling trajectory CDF to the uniform CDF.

An analytical description of $\chi$ is possible only for simple k-space trajectories, nevertheless, an approximate distribution, $\chi e$, can be computed empirically using physiologic data. For this purpose, ECG data from normal subjects are used to determine the empirical distribution, as described in the next section. In this approximation, a set of angles $S = \Delta\theta_i$ is determined for each image frame. The total number of elements of S is then $N_e = N_\theta N_f$, where $N_f$ is the total number of image frames.

A measurement of uniformity is derived from the cumulative distribution function $$CDF_i = \frac{1}{A} \sum_{i=0}^{N_e} \Delta\theta_i, \tag{10}$$

where, by definition, the normalization constant A is determined such that $$\sum_{i=0}^{N_e} CDF_i = 0.5. \tag{11}$$

The cumulative distribution function is useful in that it provides a simple, quantitative method to compare a polar sampling distribution to the ideal, uniformly spaced distribution. The relationship between approximate and ideal distributions can be expressed as the percent ideal uniformity (related to the Gini coefficient), $$P = \frac{CDF(\chi_e)}{CDF(\chi_0)}. \tag{12}$$

The percent ideal uniformity was expressed as a fraction of 100%.

In one exemplary testing, 3-lead, chest ECG data was collected from 10 normal subjects at a 400 Hz sampling rate. This data was resampled to the MRI scanner repetition time (TR). The duration of the ECG recordings was 75.7±23.7 sec, corresponding to $2.7 \pm 0.85 \times 10^4$ k-space projections sampled at TR=2.8 ms. Although, in this example, MRI data was not collected, it is possible to determine the radial angles that would be chosen from the ECG signal alone.

First, a training period was used to determine an initial array of projections. During the training period, ECG data was collected so that a sufficient number of projections could be used to compute new polar angles in one embodiment. The duration of this training period was the time necessary to acquire M k-space projections to fill the large signal buffer $S_L$ for cross-correlation and, during this time, each projection angle was assigned randomly from the interval (0-180°).

After the training period was complete, the signals were cross-correlated (Eq. [5]), a list of previously acquired polar angles was sorted and the next angle was determined (Eq. [7]). This process was repeated until the end of the ECG recording. Then, for the projections belonging to each image frame, the finite difference (Eq. [7]) was determined and the probability distribution $\chi$, cumulative distribution function CDF($\chi$) and percent ideal uniformity P were measured. The total number of measurements in the probability distribution $\chi$ was Ne=$N_\theta N_f$. These measurements were repeated for the following acquisition schema (shots-segments-projections): 1-128-65, 2-64-97, 4-8-29, 4-16-57, 4-32-117, 4-64-225, and 8-16-121. For comparison, $\chi$, CDF, and P were also measured for two pre-defined k-space trajectories: (1) golden polar angle sampling of k-space, in which the polar angle was incremented on a fixed schedule $\theta_{i+1} = \theta_i + 111.25°$ and (2) random polar sampling, in which the polar angle was determined randomly from the interval (0-180°).

For simulations, MR image data was obtained from one normal human subject and two patients with arrhythmias.

All subjects and patients gave informed consent prior to participating in the study, approved by the Institutional Review Board of the University of Pennsylvania. Image data was acquired on a 1.5 T whole-body MRI system (Avanto; Siemens Healthcare; Erlangen, Germany) equipped with a 40 mT/m gradient coil and a 32 channel RF receiver array (16 anterior and 16 posterior elements). Cardiac gating was obtained with a 3-lead wireless ECG system and logged in real-time. Time-stamps were communicated using TCP/IP from the pulse sequence to the ECG log file to synchronize image and ECG data. Left ventricular, short-axis, real-time data was obtained using a golden angle radial trajectory and image parameters, flip angle=70°, TE=1.4 ms, TR=2.8 ms, number of frequency encoded points=128, field-of-view=340 mm×340 mm, slice thickness=8 mm, bandwidth=1140 Hz/pixel. 10-40 seconds of continuous golden angle radial data was collected, resulting in 6000-20000 golden angle radial projections.

K-space signal data was reconstructed offline using a non-Cartesian SENSE algorithm in open-source software on a Linux workstation. The reconstructed image frame rate was 300 frames per second and exposure time (temporal footprint) was 95 ms (=34 projections per frame). To remove residual radial streak artifacts, a median filter was applied with a width of 30 frames. The final 128×128 images were interpolated to 512×512.

Simulated data was created using the MRI signal equation $$s(k) = \sum_{m,n=0}^{M,N} \rho(x)e^{-ik \cdot x} dx, \quad (13)$$

where s is the encoded k-space signals, N and M are the dimensions of the object (=512×512). The k-space positions k were specified by the radial sampling trajectory (random, golden or projections of one embodiment). Images were reconstructed from the simulated k-space signals using a non-Cartesian SENSE algorithm in open source software, as described above.

The mean heart rate of the 10 normal subjects was 72.2±4.7 bpm. The RR-interval varied from $\sigma_{RR}$=35.5-157.3 ms with a median variation of 59.3 ms.

Figure 7:
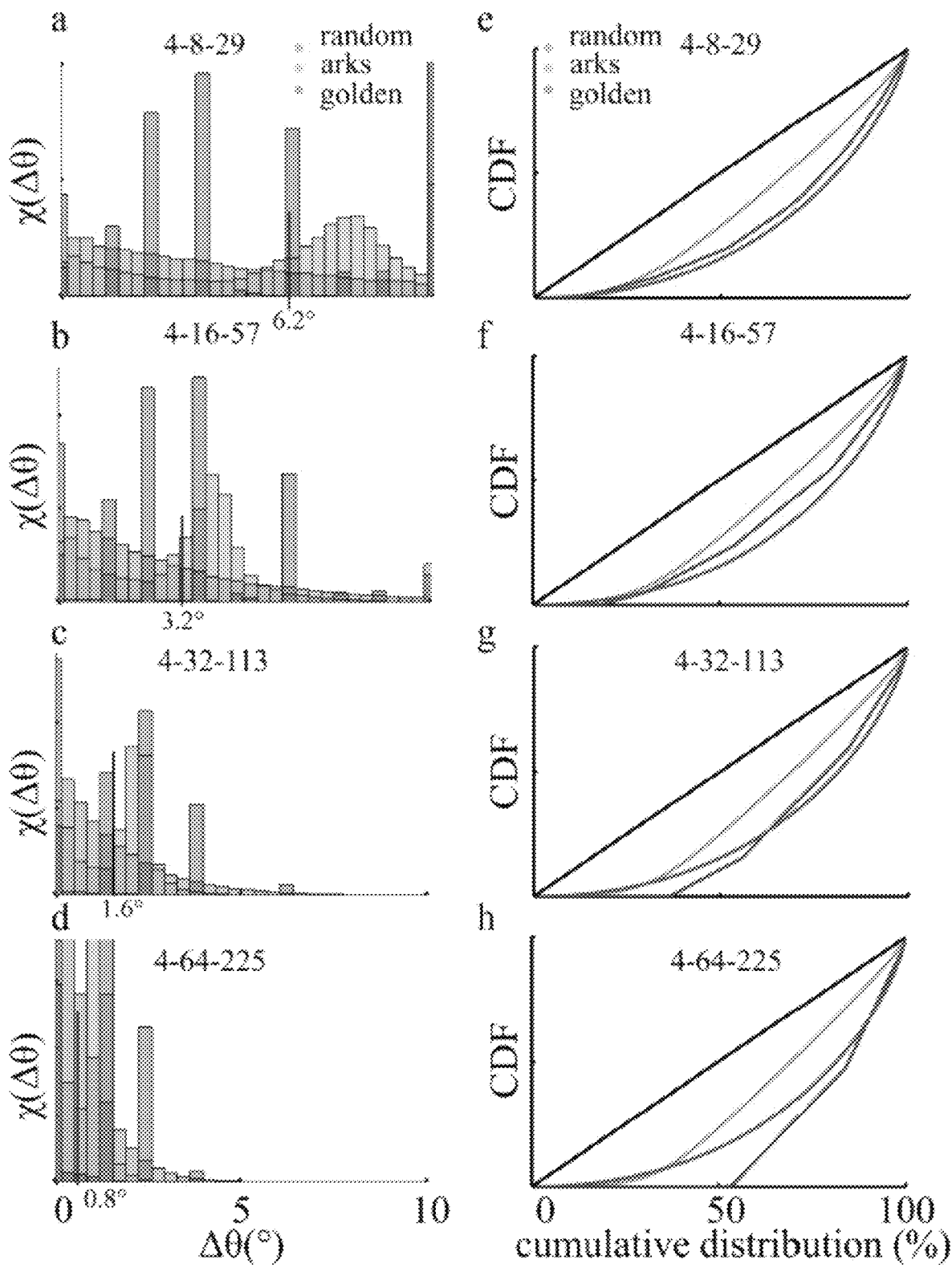
FIGS. 7A-H illustrate the probability distributions and cumulative distribution functions for 4 different sampling schemes.

For all 10 subjections, the overall probability distribution $\chi e$ was highly robust to normal ECG variations and could be qualitatively characterized by a superposition of two distributions $\chi e = \chi 1 + \chi 2$; first, a broad distribution of angles near to the ideal distribution ($\chi 1$), and a second distribution of angles at smaller polar spacing $\chi 2$ (FIG. 7A). $\chi 1$ and $\chi 2$ were present in all normal subjects. The results from a single normal subject are shown in FIG. 7. Four different sampling schemes with a fixed number of shots, but varying segments and projections, (shots-segments-projections) 4-8-29, 4-16-57, 4-32-113 and 4-64-225, are shown. The distribution was very close in comparison to the ideal distribution angle $\chi 0$=6.2°, $\chi_{1,4-8-29,max}$=7.8±0.1°. The results for other sampling schemes were consistent and are shown in Table 1. The cumulative probability distributions CDF for random and golden angle radial sampling schemes are also shown in FIG. 7.

The percent ideal uniformity for all 10 normal subjects is shown in Table 2. Overall, the present system had P=64-69% for multi-shot sampling schemes and P=94.9±0.1% for a single-shot sampling scheme (1-128-65). The percent ideal uniformity variation across all ten subjects was low (P=0.1-0.7%). In comparison, random sampling consistently was P=50-51% and golden angle sampling P=47-61%. As expected, golden angle sampling had very high single-shot percent ideal uniformity P=90.6±0.1%. CDFs for a single normal subject and for 4-shot trajectories are shown in FIGS. 7E-F.

FIGS. 7A-H show the probability distributions (FIGS. 7A-D) and cumulative distribution functions (E-H) for 4 different sampling schemes (7A and 7E, 4-8-29), (7B and 7F, 4-16-57), (FIGS. 7C and 7G, 4-32-113) and (FIGS. 7D and 7H, 4-64-225) and 3 radial sampling trajectories (random, one embodiment of present method, and golden angle sampling). The ideal distribution is labeled (black line) and angle shown.

An example of sampling for a subject with a regular arrhythmia is shown in FIG. 8. The rhythm in this subject featured a normal beat (0.76±0.03 sec), a second beat interrupted by a pre-ventricular contraction (0.36±0.02 sec), followed by a third long beat with a longer RR-interval (1.2±0.05sec). Each of the 3 beats were correctly differentiated and segmented, despite distortion of the ECG waveform by the electrohemodynamic effect of the 1.5 T MRI scanner (c.f. FIG. 8A, for which the ECG was obtained outside of the MRI scanner). Simulated images correctly depicted the tri-beat arrhythmia morphology in real-time (FIG. 8G). For both subjects, $\chi 1$ and P were within $\sigma$<1 of normal subjects (c.f. Tables 1 and 2). The present system correctly identified the cardiac phase in both arrhythmia patients and both $\chi$ and CDF were had robust performance to beat-to-beat variations in rhythm and heart rate (FIG. 9)

Figure 8A:
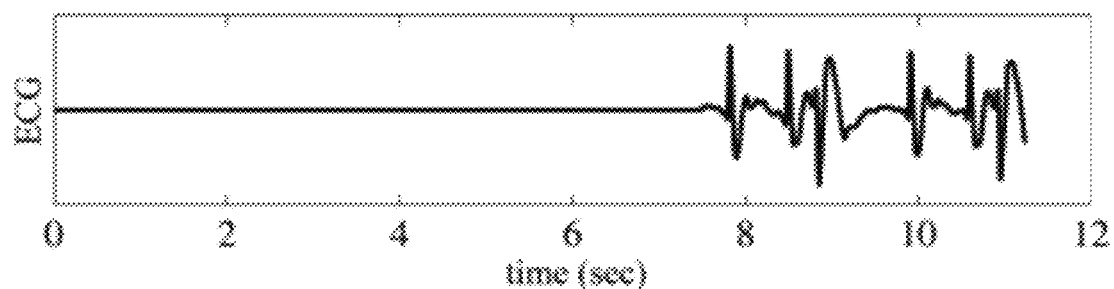
FIGS. 8A-G show adaptive radial projections for a patient with a severe arrhythmia using a 4-16-57 sampling scheme (shots-segments-projections).
Figure 8B:
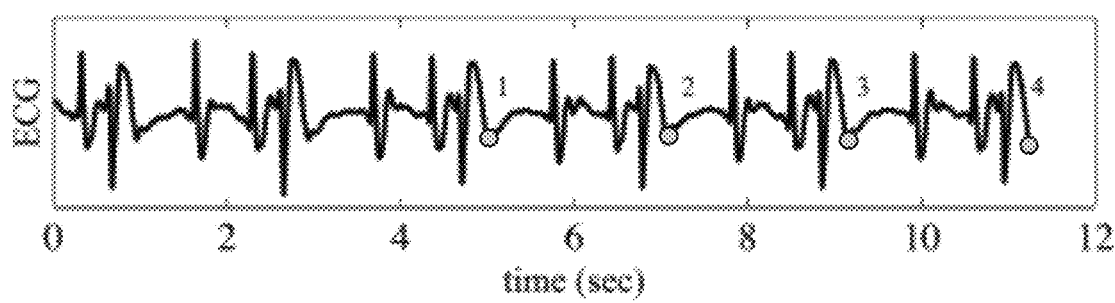
Figure 8C:
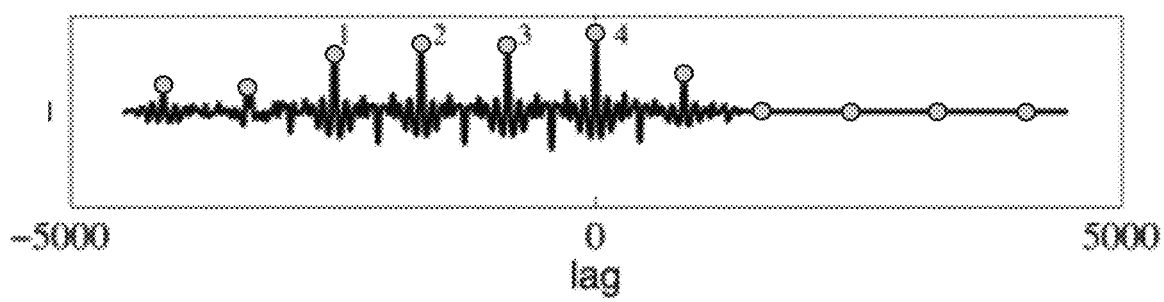
Figure 8D:
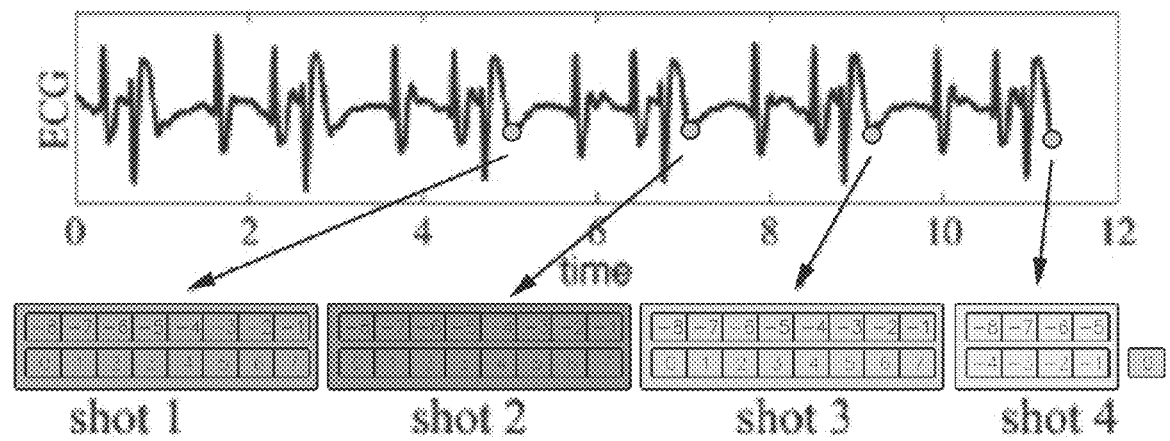
Figure 8E:
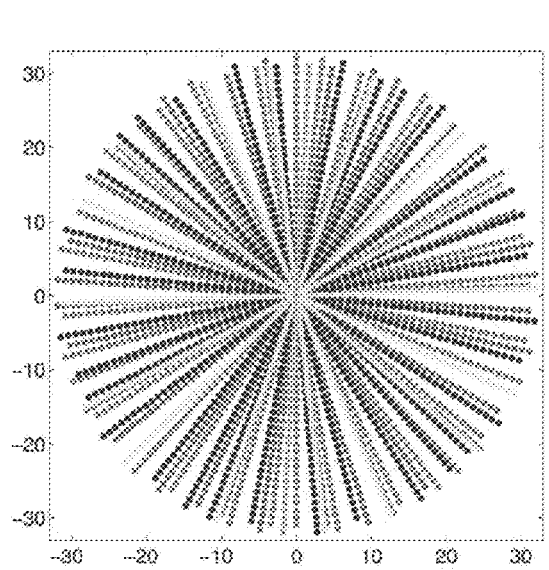
Figure 8F:
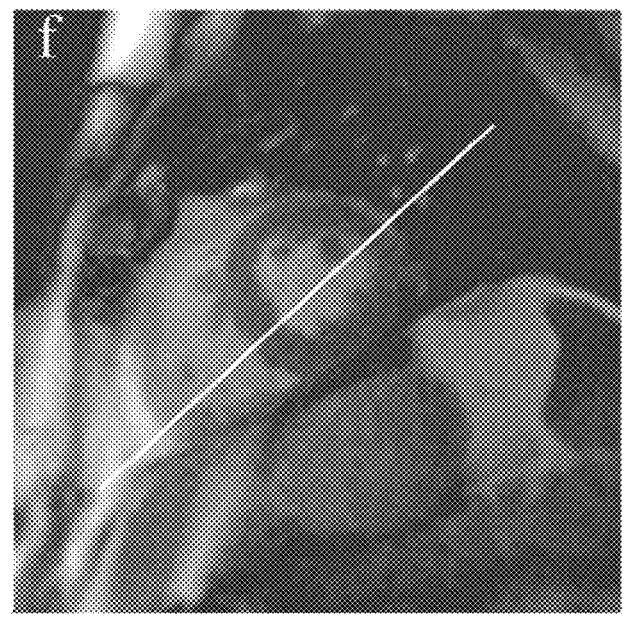
Figure 8G:
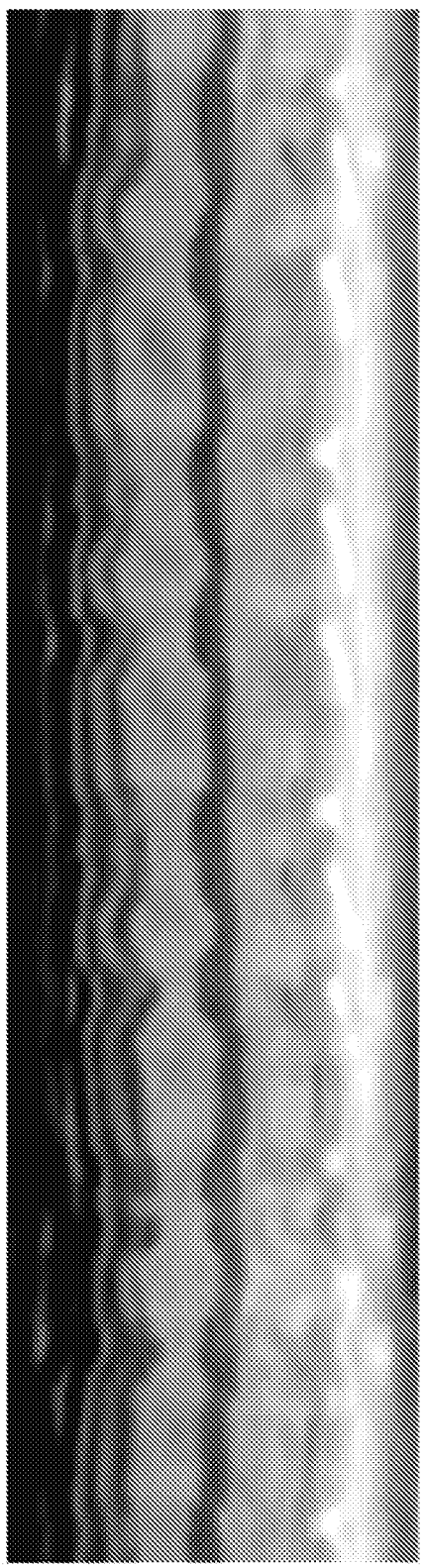
Figure 9A:
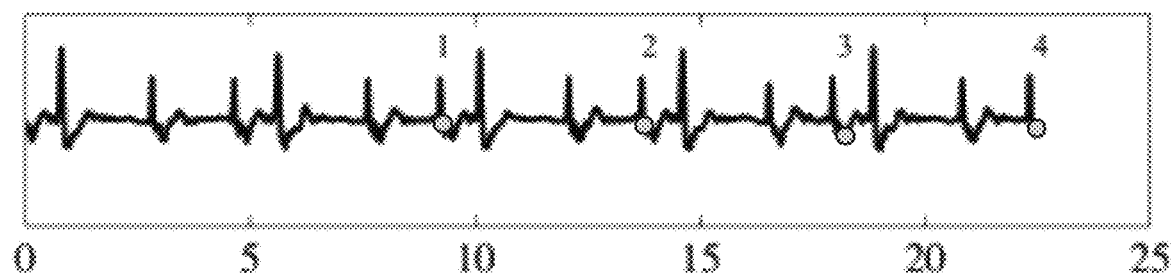
FIGS. 9A-F illustrate ECG signals, probability distribution and cumulative distribution functions CDF for a 4-32-113 radial acquisition scheme in 2 patients with abnormal heart rhythm.
Figure 9B:
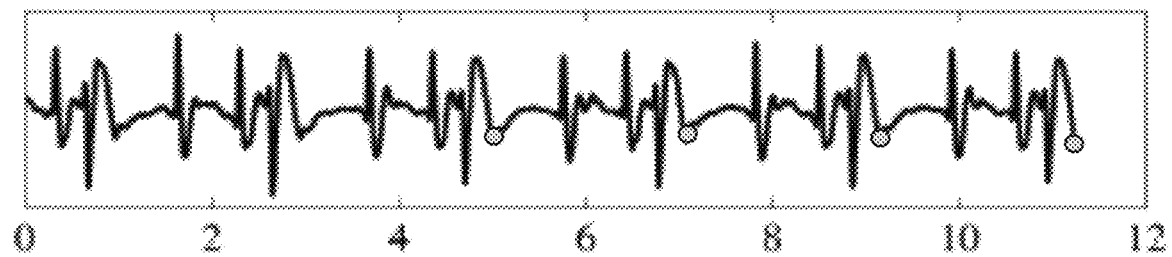
Figure 9C:
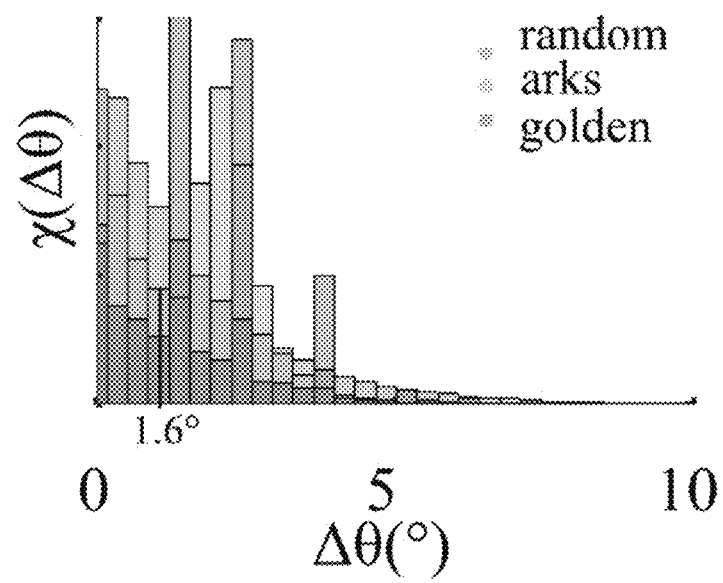
Figure 9D:
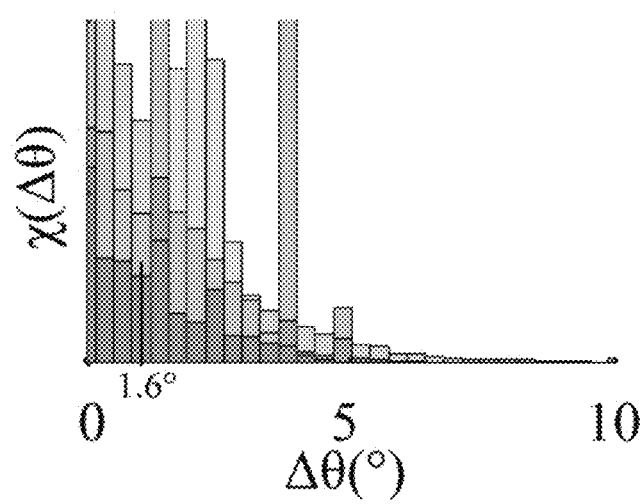
Figure 9E:
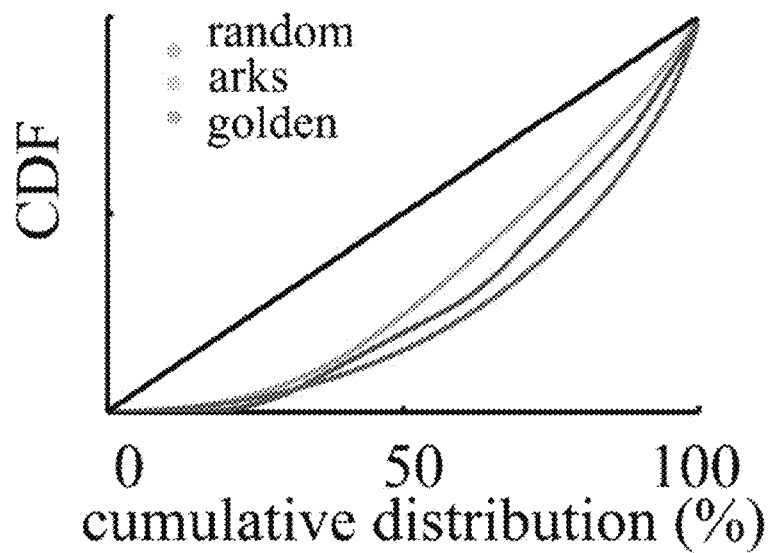
Figure 9F:
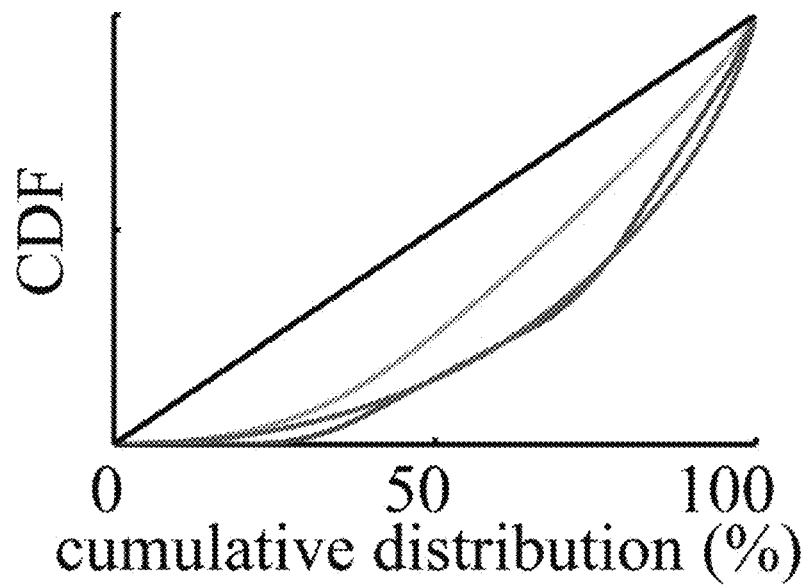

FIGS. 8A-F are diagrams that show adaptive radial projections for a patient with a severe arrhythmia using a 4-16-57 sampling scheme (shots-segments-projections). In FIG. 8A, a signal buffer SS with the most recent physiologic data (1-2 heart beats). In FIG. 8B, a large buffer SL storing a previous history of the physiologic signal. 4 similar periods of the cardiac cycle are labeled (red-lightly shaded). In FIG. 8C, cross-correlation between buffers SS and SL. Local maxima of signal overlap are labeled (red-lightly shaded). The negative lags for the first 4 local maxima are used to label the ECG in FIG. 8B. In FIG. 8D, for the first 3 shots, 16 radial projections (segments) are acquired and labeled −8 to 7, with the 0 projection corresponding to the lag index in FIG. 8C. 8 projections are acquired in the last shot and together these 56 projections are used to determine the angle θ of the 57th projection. In FIG. 8E, 57 k-space radial projections. The color of each projection corresponds to the shot index in FIG. 8D. In FIG. 8F, a simulated image from the radial projections acquired in e. g, time-varying ventricular volume is shown from the intersection (white line) in FIG. 8F. The arrhythmia can be clearly seen from the non-periodic motion of the heart in FIG. 8G (x-axis=time, y-axis=spatial projection of white line in FIG. 8F).

FIGS. 9A-F illustrate ECG signals (FIGS. 9A-B), probability distribution (FIGS. 9C-D) and cumulative distribution functions CDF (FIGS. 9E-F) for a 4-32-113 radial acquisition scheme in 2 patients (subject 1=FIGS. 9A, 9C, 9E; subject 2=FIGS. 9B,D,F) with abnormal heart rhythm.

TABLE 1

Radial sampling distributions in 10 subjects with normal sinus rhythm

| Sampling Scheme* | 1-128-65 | 4-8-29 | 4-16-57 | 4-32-113 | 4-64-225 |
|---|---|---|---|---|---|
| Ideal$\chi_{0,max}$ | 2.8 | 6.2 | 3.2 | 1.6 | 0.8 |
| ARKS$\chi_{1,max}$ | 2.7 ± 0.1 | 7.8 ± 0.1 | 4.2 ± 0.1 | 2.4 ± 0.1 | 1.0 ± 0.1 |

*shots-segments-projections

TABLE 2

Percent ideal performance P in 10 subjects with normal sinus rhythm

| | Sampling Scheme* | | | | | | |
|---|---|---|---|---|---|---|---|
| | 1-128-65 | 2-64-97 | 8-16-121 | 4-8-29 | 4-16-57 | 4-32-113 | 4-64-225 |
| Random | 50.1 ± 0.1 | 50.3 ± 0.2 | 50.2 ± 0.1 | 51.0 ± 0.1 | 50.5 ± 0.1 | 50.3 ± 0.1 | 50.1 ± 0.1 |
| Golden | 90.6 ± 0.1 | 61.7 ± 4.9 | 50.5 ± 5.6 | 57.9 ± 2.0 | 56.9 ± 3.9 | 51.9 ± 7.5 | 42.7 ± 8.4 |
| ARKS | 94.9 ± 0.1 | 68.5 ± 0.3 | 64.5 ± 0.1 | 69.1 ± 0.7 | 67.1 ± 0.6 | 65.5 ± 0.3 | 64.1 ± 0.3 |

*shots-segments-projections

Figure 10:
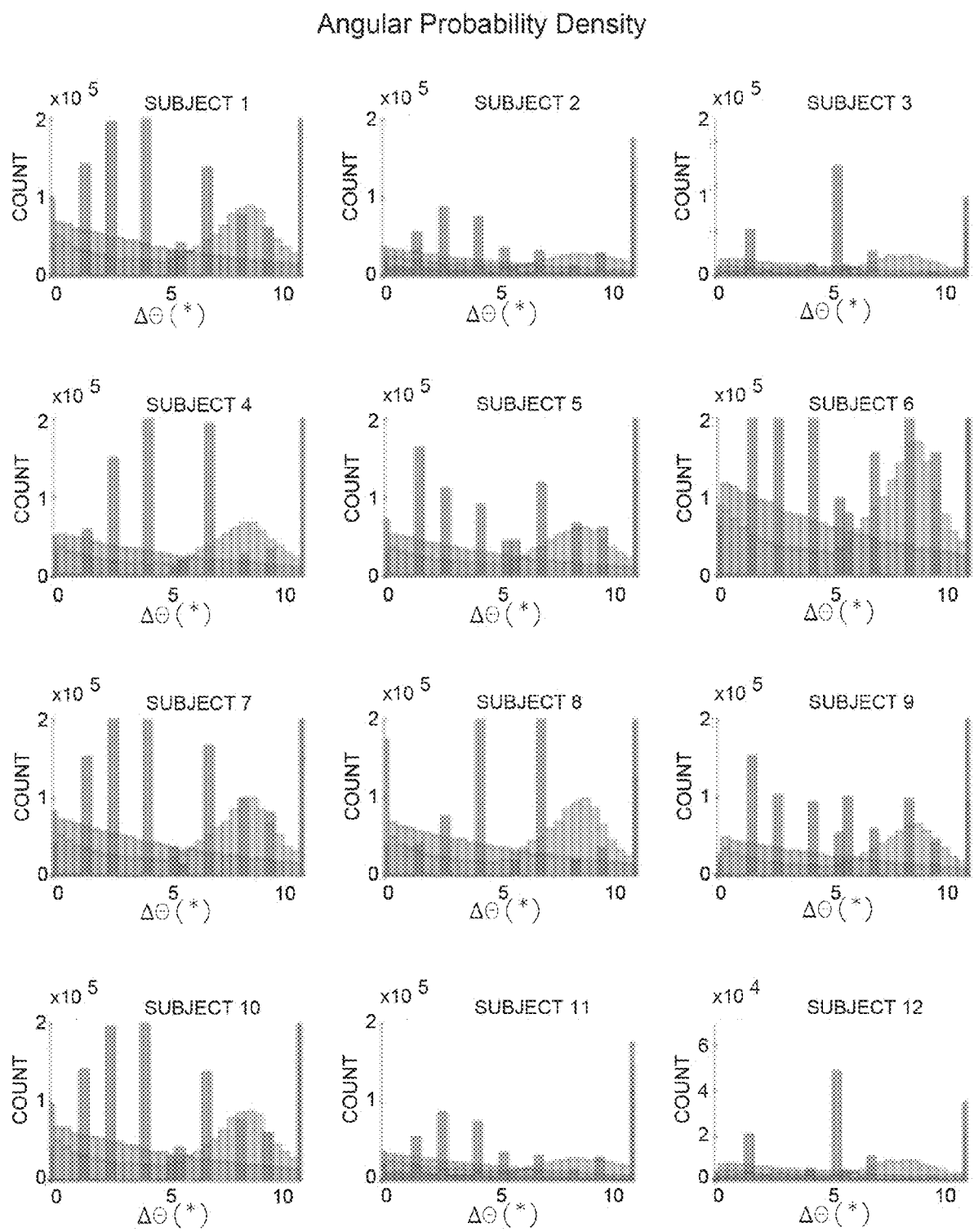
FIG. 10 illustrates probability distributions from 10 normal subjects and 2 patients

FIG. 10 shows probability distributions from 10 normal subjects (1-10) and 2 patients (11-12) using random (red), golden (blue) and ARKS sampling (green).

Figure 11:
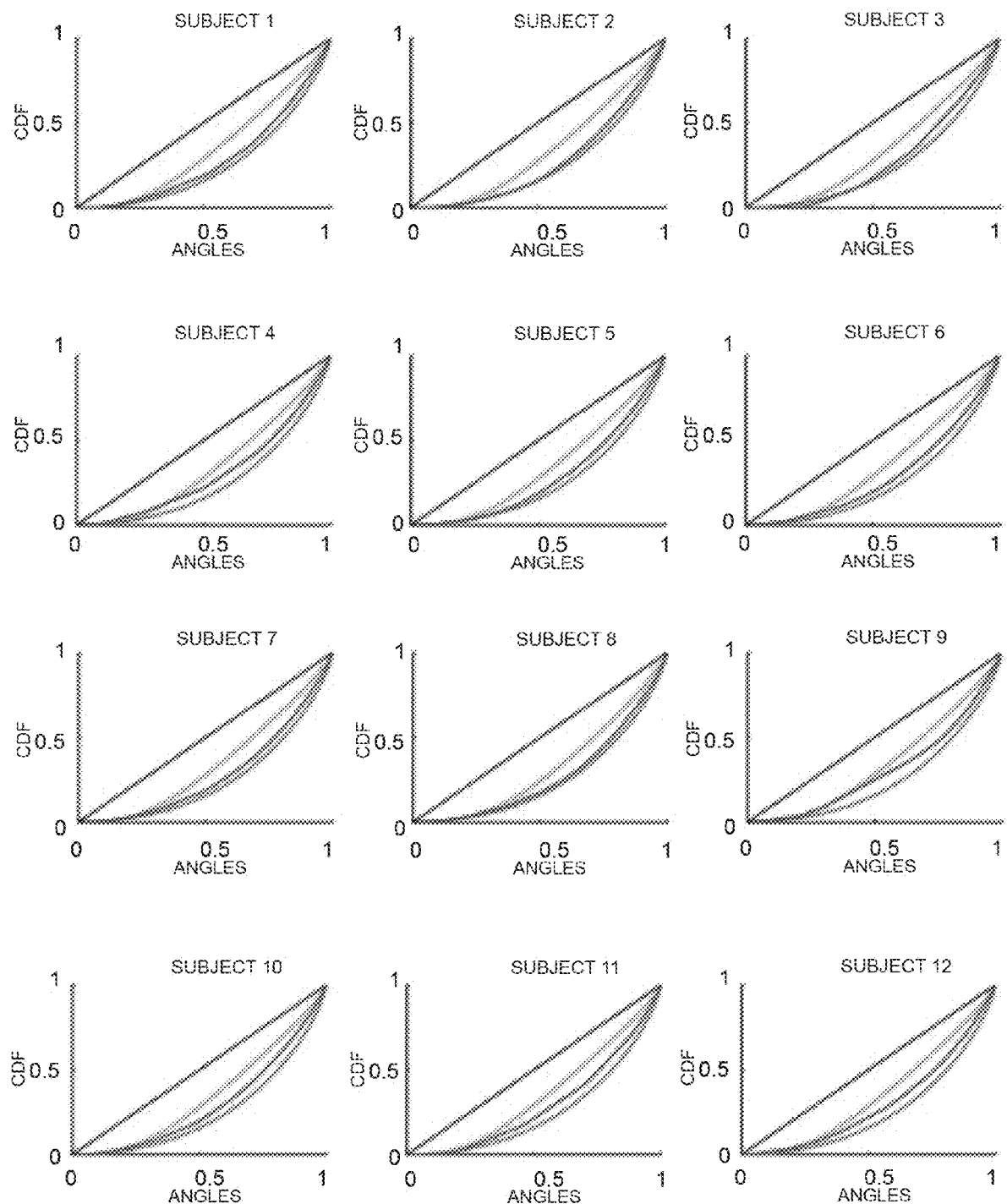
FIG. 11 illustrates cumulative distribution functions from 10 normal subjects and 2 patients.

FIG. 11 shows cumulative distribution functions from 10 normal subjects (1-10) and 2 patients (11-12) using random (red), golden (blue) and ARKS sampling (green) and uniform (black) spacing.

It will also be appreciated that the methods described herein may be implemented in software that operates on a processor that executes instructions stored in a memory component. The processor may include a standardized processor, a specialized processor, a microprocessor, or the like. The processor may execute instructions including, for example, instructions for implementing the method as described herein. On the other hand, the memory component stores the instructions that may be executed by the processor. The memory component may include a tangible computer readable storage medium in the form of volatile and/or nonvolatile memory such as random access memory (RAM), read only memory (ROM), cache, flash memory, a hard disk, or any other suitable storage component. In one embodiment, the memory component may be a separate component in communication with a processor, while in another embodiment, the memory component may be integrated into the processor. Such non-transitory memory components may be used as a computer readable storage device to store the instructions for implementing the methods and software features described herein.

Such a processor can be part of, or operably connected to, an MRI device. The MRI device can include components including the Magnet, Gradient coils, RF coils and RF detector, RF amplifier, electronic oscillator, magnetic field gradient power amplifiers, patient table, physiologic monitoring unit.

Figure 12:
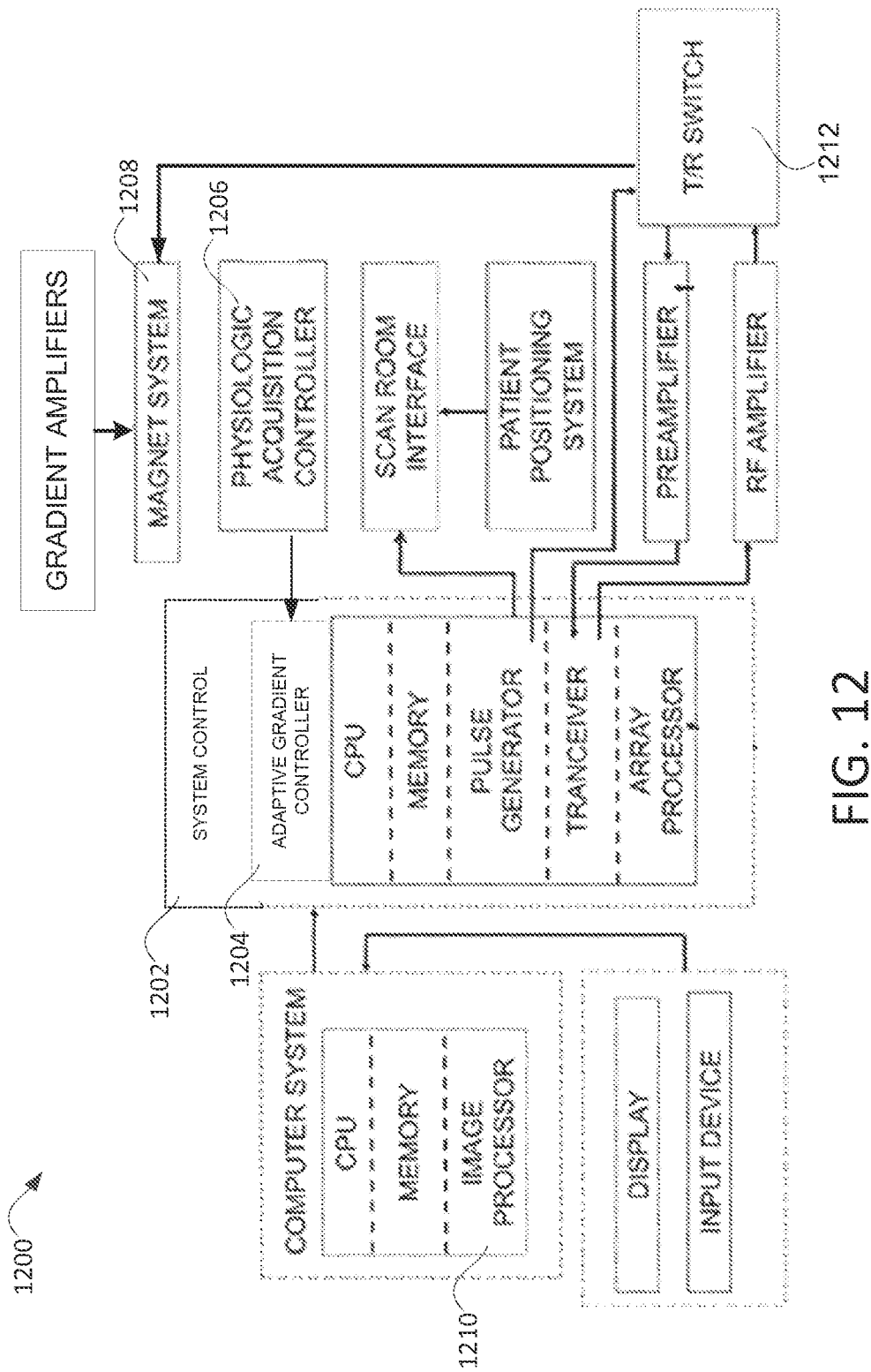
FIG. 12 is a diagram of an exemplary MRI device.

FIG. 12 is a diagram of an exemplary MRI device 1200 that can be used with the system and method described above. System control 1202 is a controller for the MRI device. System Control 1202 can include an adaptive gradient controller 1204 that can be used to determine new MRI hardware-controllable settings. The new MRI hardware-controllable settings can be determined by analyzing physiologic data to determine at least one previous time that the body part was in a similar position to the current position and by analyzing MRI hardware-controllable settings used at the at least one previous time to determine new MRI hardware-controllable settings. A physiologic acquisition controller 1206 can include or be associated with a sensor to obtain physiologic data, such as heart data like an ECG.

An MRI scanner can scan the body part with the new MRI hardware-controllable settings to produce new MRI data. The MRI scanner can include magnet system 1208 and Transmit/Receive (T/R) switch 1212. An image processor 12010 can be used to produce the MRI image using the new MRI data.

Additional Description

In one embodiment, a system for continuous adaptive cardiovascular magnetic resonance (CMR) is described.

Technologies are desired to dramatically improve spatial resolution, sensitivity and specificity of MRI to detect AR myocardium. Motion compensation in MRI is essential to reduce artifacts, improve spatial resolution and coverage, yet there are no methods in which 3D data can be collected across a very large number of heartbeats (minutes), but, at any given moment, a uniformly-sampled k-space would be potentially available for image reconstruction from consistent motional data. Continuous adaptive sampling is a method that may improve MRI spatial resolution and reduce motion artifacts by responding to physiologic signal changes rapidly. A high-performance continuous adaptive system on a clinical MRI scanner for assessment of Left Ventricular (LV) function in cine MRI applications is validated.

Technologies are desired to improve the spatial coverage and spatiotemporal resolution of cine MRI to better assess cardiovascular disease. A continuous adaptive MRI system to improve image quality and obtain real-time images from a segmented, radial cine acquisition is implemented. In neuroimaging applications, prospective motion correction using navigators in image-63,64 or k-space, or using external tracking devices have the potential to improve image quality during 3D scans, but these systems have limited applicability to body organs because of non-rigid cardiac and respiratory motion and because the use of external motion tracking devices to detect cardiac phase has clear drawbacks.

The principal difference between this system and view-sharing radial cine is that adaptive MRI prospectively updates the radial view angle in real-time (each TR; i.e. within 3 msec) and can analyze an ECG waveform to guarantee consistent view sharing in segmented mode. View-shared, segmented radial cine reconstructs images only when the entire scan is complete, but adaptive MRI can reconstruct an image as often as each new radial view is acquired, since the segmented data is consistent and view angles have uniform angular distribution in k-space. One application of this technology is the generation of 3D cine MRI images in real-time.

Example: Real-time Cine MRI. A physiologic signal, such as the ECG, is continuously matched to previously acquired signals obtained during the same examination using autocorrelation (see FIG. 8A-G for further details). The signal should be at least quasi-periodic for a similar, previously acquired signal to be found. After one or more matched signals are found, a list of the previously acquired angular views θ is determined, the largest angular gap in k-space is found and a new angle is determined that bisects this gap. This calculation is done for each acquired radial view and, for real-time cine bSSFP, the trajectory is continuously adapted each TR (<3 msec). This method allows for realtime MRI data to be collected and displayed in segmented mode from a radial acquisition.

Basic Principles. In one embodiment, the four basic principles of continuous adaptive MRI are a) to dynamically respond to or anticipate physiologic signals in realtime; b) guarantee data consistency among distinct periods of the MR examination; c) maximize data usage efficiency; and d) have sufficient data to produce a useful image in real-time.

1. Dynamic response. In general, a physiologic signal is used as an input to determine the future amplitudes of the spatial encoding magnetic field gradients G and RF pulses. The physiologic signal could be any type of signal from the patient, such as an estimate of the current cardiac or respiratory phase, a response from the patient to stress challenge, or it could be the current position of a catheter in an artery for interventional MRI. The physiologic signal could be derived from an external measurement device such as an ECG or it could be derived from real-time image data using self-gating. Whatever the source of the physiologic signal, the imaging system is prepared to respond to it with a new set of instructions. An extension is the ability to anticipate the physiologic signal.

Anticipation or forecasting is possible using time series analysis or control theory when the behavior of the dynamical system is known or can be estimated. One method to anticipate the signal is autoregressive moving average models, as proposed in Aim 3.

2. Data consistency. For quasi-periodic signals, it is advantageous to guarantee that the data is consistent from period to period if it is to be combined for image reconstruction. A pattern-matching analysis is performed on the physiologic data to determine possible candidates for data consistency. Pattern-matching can evaluate the maximum overlap (inner-product) of a two physiologic signal, perform an autocorrelation between the most recent data and the signal history, or it could estimate the minimum Euclidean distance between multiple labels derived real-time image data and warped using image registration. In a prototype system, ECG signal autocorrelation is performed to infer consistent cardiac phases.

3. Data efficiency. MR image reconstruction generally requires Nyquist sampling to be fulfilled so that the MR signals do not result in signal aliasing or radial streaking. Even when multiple detectors or compressed sensing is used to generate an image from less data than would be required by Nyquist, it is generally better to use as much consistent data as possible, when available, to improve the signal-to-noise ratio.

4. Real-time. A final requirement for continuous adaptive MRI is that sufficient information is available to reconstruct an image in real-time (e.g. a new image could be produced each TR with this system).

Figure 13:
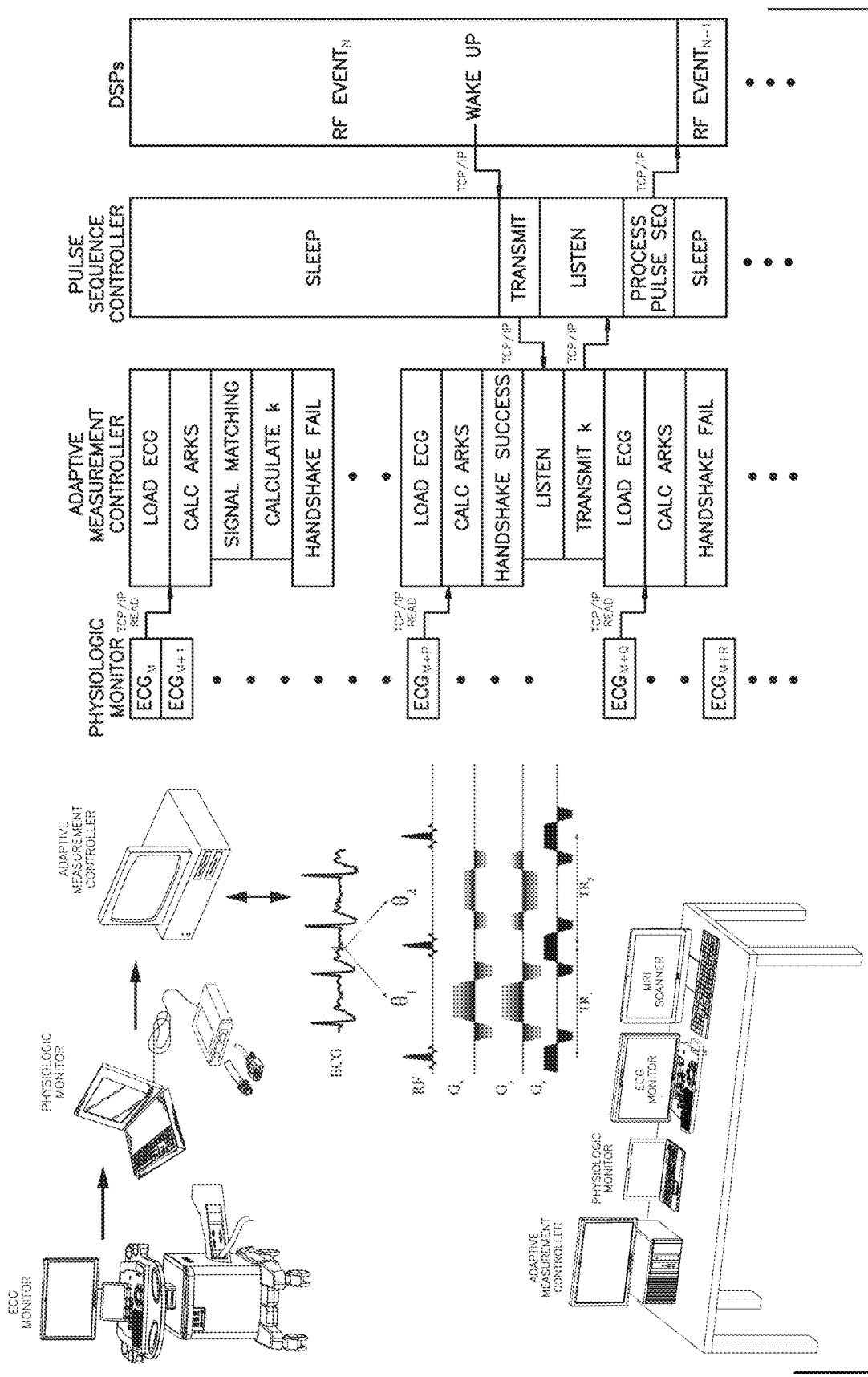
FIG. 13 illustrates a calculation of a new radial angle using continuous adaptive MRI.

In an illustrative test, a prototype continuous adaptive MRI system was interfaced to a whole-body clinical MRI scanner using an adaptive 2D segmented radial cine trajectory (as detailed below and in FIG. 8A-G). The prototype provides four systems for real-time communication and feedback (FIG. 13). Three systems are well known to engineers of MRI devices: the physiologic monitor, pulse sequence and digital signal processors. Continuous adaptive MRI provides one new component called the adaptive measurement controller.

Physiologic Monitor. The physiologic monitor can receive physiologic signals from the patient. The physiologic signal used in the prototype is the ECG waveform obtained from a 3-lead wireless ECG device.

Adaptive Measurement Controller. The adaptive measurement controller can be hardware or software that analyzes a physiologic signal and provides feedback to the pulse sequence. In the prototype system, the adaptive measurement controller continuously autocorrelates the ECG signal to find consistent cardiac phase information and calculate a new radial view angle each TR (in<3 msec) based on previously acquired data.

Pulse Sequence. The pulse sequence controller can be hardware or software that processes pulse sequence instructions. The pulse sequence instructions are the timing events, amplitudes and frequencies for RF pulses, magnetic fields gradients, data sampling and more.

Digital Signal Processors. The digital signal processors can transform the digital instructions received from the pulse sequence controller to analog signals that are delivered to hardware (e.g. currents in magnet coils).

In one embodiment, multiple Modes of Operation can be used including standby mode, training mode and active mode.

1. Standby Mode In standby mode, the physiologic monitor and adaptive measurement controller store and analyze physiologic data in preparation for the MRI scan to start. The physiologic monitor continuously logs patient physiologic data and transmits it via TCP/IP to the adaptive measurement controller, which stores data in a memory buffer. The pulse sequence controller and DSPs are not active at this time.

2. Training Mode. Training mode begins when the pulse sequence initiates a handshake with the adaptive measurement controller. During pulse sequence preparation, the handshake event is communicated between the two services. The adaptive measurement controller detects that a handshake was initiated and reciprocates by transmitting a training k-space trajectory. Training mode is concluded when the adaptive measurement controller has collected sufficient data to adaptively respond to the physiologic data with a new optimized trajectory.

3. Active Mode. The pulse sequence adaptively responds to physiologic feedback and provides real-time sampling, reconstruction and display in active mode. The timing information of this complex process can be represented by the event-timing diagram, which depicts the sequence of events and interactions between the physiologic monitor, the adaptive measurement controller, the pulse sequence and digital signal processors (DSPs) (FIG. 13).

Active mode commences when the memory buffers are completely filled in training mode. In active mode, the adaptive measurement controller performs 3 steps sequentially: a) It checks for a handshake from the pulse sequence and, if a handshake is received, then the pulse sequence is updated and, otherwise, there is a timeout event; b) New ECG data is read and stored into memory; c) The ECG data is analyzed and a new k-space trajectory k is calculated. Meanwhile, the pulse sequence, having transmitted the handshake, listens for k from the adaptive measurement controller. When k is received, the pulse sequence transmits the new instructions to the DSPs and waits for a wakeup instruction. After the wakeup instruction is received, a handshake event is transmitted back to the adaptive measurement controller and the process repeats.

Updating the radial view angle An implementation of continuous adaptive MRI for radial sampling is shown in FIG. 8. In FIG. 8A, the most recent physiologic signal $S_S$ is stored in a small buffer in memory. The size of the buffer is chosen to capture important features of the signal, such as the R-wave. In FIG. 8B, a larger signal SL containing a previous record of the physiologic data is stored in a M×1 buffer in memory. The front of the vector SS is zero-padded to length M, the same length as the larger buffer. The signals are time-reversed and cross-correlated $$(S_L * S_S)[n] = \sum_{i=0}^{M-1} S_S^*[m]S_L[m+n].$$

Local maxima are determined from the result of the cross-correlation as shown in FIG. 8C and correspond to the signals highlighted in red in FIG. 8B. The lag of each local maxima is an index to the maximum overlap of the two signals. Data sampling across multiple heartbeats is specified by the number of radial views (segments) per heartbeat (shot). An example of how segments and shots are defined is shown in FIG. 8D. In the example shown, the number of segments is 8 and the number of shots is 4.

The total number of views is Nviews=Nshots*Nsegments−Nsegments/2+1. For each shot, the lag corresponding to the local maxima is the center of the segments of k-space views used. From a list of previously acquired projections, the angle corresponding to the identified segments are collated. The list is sorted in ascending order, from zero to 360 degrees, and finite differences are computed from all angles. The maximum angular difference is bisected by the next projection (FIG. 8E). To guarantee real-time performance, the mean per-step calculation time was estimated with a c++ profiler: 1) ECG TCP/IP socket read and buffer storage is 11 μs, 2) updating the radial view angle ('calc arks' in FIG. 13) was 160 μs, 3) angle transmission to the pulse sequence via Transmission Control Protocol/Internet Protocol (TCP/IP) was 17 μs, and 4) other software overhead was <5 μs. Step 2, cross-correlation of the ECG signal (16 seconds ECG data sampled at 400 Hz), well below the TR of the balanced steady-state free precession (bSSFP) sequence.

FIG. 13 illustrates a calculation of a new radial angle using continuous adaptive MRI. Physiologic (ECG) data is continuously measured and transmitted via TCP/IP to the adaptive measurement controller. Upon receiving update of the ECG buffer, crosscorrelation of the recent physiologic history is performed to find the most consistent sampled data across multiple shots and calculate a new angle for the next TR of a radial bSSFP acquisition. Continuous adaptive measurement is performed as an asynchronous process with the pulse sequence controller, which sleeps while the digital signal processors execute hardware commands.

Perform testing and validation of continuous, adaptive MRI. Images can be acquired on a MRI system such as a 1.5 T whole-body MRI system (Avanto; Siemens Healthcare; Erlangen, Germany) equipped with 40 mT/m gradient coil and a 32 channel RF receiver array (16 anterior and 16 posterior elements). For real-time scans, cardiac gating can be performed with a 3-lead wireless ECG system. ECG data can be logged in real-time and time-stamps communicated using TCP/IP from the pulse sequence to the ECG log file to synchronize image and ECG data. 2D LV, short-axis and 4 chamber, real-time data can be obtained using continuous adaptive sampling with acquisition parameters at an in-plane spatial resolution of 1.5-2.5 mm2 and slice thickness=6-8 mm. Image data can be reconstructed online using a non-Cartesian SENSE algorithm on a Linux workstation. The reconstructed image frame rate can be approximately 60 fps, with a range of shots and segments to vary exposure time (temporal footprint). For comparison, retrospective cine MRI images can be obtained in breath-held mode with matched field-of-view and in-plane spatial resolution. LV volumes and 6-segment myocardial displacements can be computed using software (CMR42, Circle Cardiovascular).

Develop a continuous adaptive trajectories for 3D and free-breathing real-time cine MRI. A 3D cine continuous adaptive MRI scan can be simulated, developed and optimized A 3D radial trajectory can be used with new angles determined from 2D finite differences in the polar (θ) and azimuthal (φ) domain (a subset of R2). In direct analogy to the 2D finite difference calculation, the 3D finite difference can seek to choose a new radial view that bisects the largest gap in R2. Free-breathing scans can be developed by transmitting navigator and self-gating signals from images Those skilled in the art also will readily appreciate that many additional modifications are possible in the exemplary embodiment without materially departing from the novel teachings and advantages of the invention. For example, the method may be modified to separately reconstruct or to motion correct for artifacts caused by respiratory motion. It will also be appreciated that the techniques described herein need not be limited to cardiac imaging but may also be used to provide more robust and faster imaging of patients in sinus rhythm. Also, longer scans may be used to allow for more fine-tuned selection of beats. In addition, different types of beats may be reconstructed separately. The use of image-derived measures of cardiac motion besides ventricular segmentation is intended to be included within the scope of this invention. For example, in the case of long-axis cardiac imaging, measurement of the width of the ventricle or the opening and closing of the aortic and mitral valves can be utilized to estimate cardiac phase. Furthermore, more automated measurements such as an image similarity metric can be utilized to improve the processing time of the method. Accordingly, any such modifications are intended to be included within the scope of this invention as defined by the following exemplary claims.

What is claimed is:

1. A method of making a Magnetic Resonance Imaging (MRI) image of a body part that undergoes at least quasi-periodic motion, the method comprising:
obtaining first physiologic data of the body part via a physiological sensor as the body part undergoes the at least quasi-periodic motion;
scanning the body part using first MRI hardware-controllable settings to produce first MRI data, wherein scanning the body part using the first MRI hardware-controllable settings is performed contemporaneous with obtaining the first physiologic data of the body part;
obtaining second physiologic data of the body part as the body part undergoes the at least quasi-periodic motion;

comparing the second physiologic data to the first physiologic data, independent of the first MRI data, to determine at least one instance in which the first physiologic data of the body part obtained during the at least quasi-periodic motion corresponds to the second physiologic data;

determining second MM hardware-controllable settings based on the first MRI hardware-controllable settings used during the at least one instance;

scanning the body part with the second MRI hardware-controllable settings to produce second MRI data; and producing the MRI image using the second MRI data.

2. The method of claim 1, wherein the body part is a heart, and the physiologic data is a heart signal.

3. The method of claim 2, wherein the physiologic sensor is an electrocardiogram (ECG) sensor.

4. The method of claim 1, wherein an autocorrelation on the physiologic data is done to determine the at least one previous instance.

5. The method of claim 1, wherein the first and second MRI hardware-controllable settings are settings to control magnetic fields and radiofrequency pulses of the MRI and correspond to k-space values of a time domain MRI signal.

6. The method of claim 5, wherein the second MRI hardware-controllable settings are such that the k-space values for the second MRI hardware-controllable settings differ from the k-space values for the first MRI hardware-controllable settings.

7. The method of claim 1, wherein the second MRI data along with the first MRI data from the at least one previous instance is used to produce the MRI image.

8. The method of claim 1, wherein the MRI image is a frame in an MRI cine.

9. A Magnetic Resonance Imaging (MRI) device configured to make an MRI image of a body part that undergoes at least quasi-periodic motion, the MRI device comprising:

a sensor configured to obtain first physiologic data of the body part as the body part undergoes the at least quasi-periodic motion;

a controller configured to compare the first physiologic data with a current position of the body part to determine at least one previous instance that the body part was in a position obtained during the at least quasi-periodic motion that corresponds to the current position of the body part;

an MRI scanner configured to scan the body part with first MRI hardware-controllable settings contemporaneous with the sensor obtaining the first physiologic data, wherein the MRI scanner is configured to produce first MRI data based on the scan of the body part with the first MRI hardware-controllable settings, wherein the controller is configured to compare the first physiologic data with the current position of the body part independent of the first MRI data and is further configured to select second MRI hardware-controllable settings based on the first MRI hardware-controllable setting used during the at least one previous instance, and the MRI scanner is further configured to scan the body part with the second MRI hardware-controllable settings so as to produce second MRI data; and an image processor configured to produce the MRI image using the second MRI data.

10. The MRI device of claim 9, wherein the body part is a heart, the sensor is a heart sensor, and the physiologic data is a heart signal.

11. The MRI device of claim 9, wherein the physiologic data is data obtained from an electrocardiogram (ECG).

12. The MRI device of claim 9, wherein the controller is configured to perform an autocorrelation on the physiologic data to determine the at least one previous instance.

13. The MRI device of claim 9, wherein the first MRI hardware-controllable settings are settings to control magnetic fields and radiofrequency pulses of the MRI scanner and correspond to k-space values of a time domain MRI signal.

14. The MRI device of claim 13, wherein the second MRI hardware-controllable settings are such that the k-space values for the second MRI hardware-controllable settings differ from the k-space values for the first MRI hardware-controllable settings.

15. The MRI device of claim 9, wherein the second MRI data along with the first MRI data from the at least one previous instance is used to produce the MRI image.

16. The MRI device of claim 9, wherein the MRI image is a frame in an MRI cine.

17. A method of making a Magnetic Resonance Imaging (MRI) image of a heart that undergoes at least quasi-periodic motion, the method comprising:

obtaining first physiologic data of the heart from an electrocardiogram (ECG) as the heart undergoes at least quasi-periodic motion;

during obtaining the first physiologic data, scanning the heart using first MRI hardware-controllable settings to produce first MRI data, wherein the first MRI hardware-controllable settings correspond to radial k-space projection angles of a time domain MRI signal;

comparing a current position of the heart based on data from the electrocardiogram (ECG) to a position of the heart obtained during the at least quasi-periodic motion to determine at least one previous instance that the position of the heart obtained during the at least quasi-periodic motion corresponds to the current position of the heart;

selecting second MRI hardware-controllable settings based on the first MRI hardware-controllable settings used during the at least one previous instance, wherein the second MRI hardware-controllable settings correspond to at least one additional radial k-space projection angle;

scanning the heart with the second MRI hardware-controllable settings to produce second MRI data; and producing the MRI image of the heart using the second MRI data.

18. The method of claim 17, wherein an autocorrelation on the physiologic data is done to determine the at least one previous instance.

19. The method of claim 17, wherein the first and second MRI hardware-controllable settings are settings to control magnetic fields and radiofrequency pulses of the MRI and correspond to k-space values of a time domain MRI signal.

20. The method of claim 17, wherein the second MRI data along with the first MRI data from the at least one previous instance is used to produce the MRI image.

* * * * *

UNITED STATES PATENT AND TRADEMARK OFFICE
CERTIFICATE OF CORRECTION

| | |
|---|---|
| PATENT NO. | : 12,004,882 B2 |
| APPLICATION NO. | : 15/522098 |
| DATED | : June 11, 2024 |
| INVENTOR(S) | : Walter R. T. Witschey et al. |

It is certified that error appears in the above-identified patent and that said Letters Patent is hereby corrected as shown below:

In the Specification

Column 1, Line 9-12, Replace:
"This application claims the benefit of U.S. Provisional Application No. 62/073,183 entitled "Method and Device for Magnetic Resonance Imaging Data Acquisition Guided by Physiologic Feedback", filed Oct. 31, 2014."
With:
--This application is the National Stage Application of International Patent Application No. PCT/US2015/057581, filed Oct. 27, 2015, which claims the benefit of U.S. Provisional Application No. 62/073,183 entitled "Method and Device for Magnetic Resonance Imaging Data Acquisition Guided By Physiologic Feedback", filed Oct. 31, 2014, the entirety of which is incorporated herein by reference.--

Column 1, Line 15-19, Replace:
"The subject matter disclosed herein was made with government support under award number R00-HL108157 awarded by the National Heart, Lung and Blood Institute, the National Institutes of Health. The Government has certain rights in the herein disclosed subject matter"
With:
--This invention was made with government support under grant number HL108157 awarded by the National Institutes of Health. The government has certain rights in the invention.--

Column 3, Line 18, Replace:
"patients"
With:
--patients.--

Column 6, Line 33, Replace:
"is that is that"

Signed and Sealed this
Fourth Day of November, 2025

John A. Squires
*Director of the United States Patent and Trademark Office*

With:
--is that--

Column 7, Line 23, Replace:
"gradients"
With:
--gradients of--

Column 9, Line 19, Replace:
"$\Delta\theta_i = \theta_{i+1} - \theta i$"
With:
--$\Delta\theta_i = \theta_{i+1} - \theta i$.--

Column 10, Line 65, Replace:
"(0-180°."
With:
--(0-180°).--

Column 12, Line 14, Replace:
"(E-H)"
With:
--(FIGS. 7E-H)--

Column 12, Line 15, Replace:
"(7A"
With:
--(FIGS. 7A--

Column 12, Line 15, Replace:
"(7B"
With:
--(FIGS. 7B--

Column 12, Line 37, Replace:
"(FIG. 9)"
With:
--(FIG. 9).--

Column 15, Line 7, Replace:
"FIG."
With:
--FIGS.--

CERTIFICATE OF CORRECTION (continued)
U.S. Pat. No. 12,004,882 B2

Column 16, Line 4, Replace:
"FIG."
With:
--FIGS.--

Column 18, Line 29, Replace:
"images"
With:
--images.--

In the Claims

Column 19, Claim 1, Line 7, Replace:
"MM"
With:
--MRI--